(12) United States Patent
Baynham

(10) Patent No.: US 12,733,960 B1
(45) Date of Patent: Sep. 15, 2026

(54) MODULAR PEDICLE SCREW ASSEMBLY

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 0 days.

(21) Appl. No.: 19/310,215

(22) Filed: Aug. 26, 2025

(51) Int. Cl.
*A61B 17/70* (2006.01)
*A61B 17/86* (2006.01)
*A61B 17/68* (2006.01)

(52) U.S. Cl.
CPC ...... *A61B 17/7071* (2013.01); *A61B 17/7032* (2013.01); *A61B 17/861* (2013.01); *A61B 2017/681* (2013.01)

(58) Field of Classification Search
CPC ............ A61B 17/7071; A61B 17/7032; A61B 17/7034; A61B 17/7037; A61B 17/7001; A61B 17/861; A61B 2017/681
USPC .......................................... 606/264–272, 279
See application file for complete search history.

(56) References Cited

U.S. PATENT DOCUMENTS

| | | | | |
|---|---|---|---|---|
| 11,020,150 B1* | 6/2021 | Doubler | A61B 17/7032 | |
| 2008/0015597 A1* | 1/2008 | Whipple | A61B 17/7037 | 606/250 |
| 2018/0221162 A1* | 8/2018 | Baynham | A61B 17/7037 | |
| 2022/0313332 A1* | 10/2022 | Jackson | A61B 17/7032 | |
| 2023/0225768 A1* | 7/2023 | Jackson | A61B 17/7038 | 606/266 |
| 2023/0404638 A1* | 12/2023 | Leff | A61B 17/7032 | |
| 2025/0049479 A1* | 2/2025 | Vedula | A61B 17/70 | |
| 2025/0375222 A1* | 12/2025 | Jackson | A61B 17/7035 | |

* cited by examiner

*Primary Examiner* — Eduardo C Robert
*Assistant Examiner* — Christina Negrellirodriguez
(74) *Attorney, Agent, or Firm* — McHale & Slavin, P.A.

(57) ABSTRACT

A modular pedicle screw assembly having a pedicle screw shank with an insertion end for vertebral engagement and a connector end with a conical outer surface and an internal driver receptacle. A spherical collet with compression slits is mounted on the connector end, the collet having upper and lower openings for driver tool access. A split ring with a chamfered lower inner edge and an overlying cap are positioned over the collet. A saddle coupled to the collet defines a U-shaped channel for receiving a spinal rod and a threaded section for a set screw. Tightening the set screw compresses the cap and split ring to lock the rod and saddle while enabling the collet to provide a polyaxial or uniplanar connection between the screw shank and the rod. The modular configuration allows insertion through minimal incisions, improves surgical and provides secure, adjustable fixation for spinal stabilization.

14 Claims, 38 Drawing Sheets

480
425
490
450
432

425
490
470
414

425
490
450
470
414
430

576
572
574
550
532

529
570
588
514

570
532
514
530

MODULAR PEDICLE SCREW ASSEMBLY

FIELD OF THE INVENTION

The present invention relates to surgical implants for spinal stabilization, and more particularly to a modular pedicle screw assembly.

BACKGROUND OF THE INVENTION

Pedicle screw assemblies are widely used in spinal surgery to provide internal fixation of the vertebrae. The pedicle screws are typically inserted through the pedicle of a vertebra and anchored within the vertebral body, allowing attachment to rods or other stabilization devices. The primary function of pedicle screws is to maintain proper spinal alignment and stability during the healing period following procedures such as spinal fusion, deformity correction, or fracture repair. By rigidly coupling adjacent vertebrae, pedicle screws facilitate bone graft incorporation and long-term spinal stability.

Despite their widespread clinical success, conventional pedicle screw systems present certain limitations. Insertion of the screw requires precise alignment to avoid damage to neural structures and to ensure secure engagement with the bone. Misalignment or suboptimal placement may compromise fixation strength or result in nerve injury. Moreover, once implanted, the screw-to-rod connection often requires additional hardware that can be bulky, difficult to assemble in confined surgical fields, or prone to loosening under biomechanical loads. Further, during installation, it can be difficult to align connecting rod members to saddle mounted pedicle screws if the saddles are freely moving.

In minimally invasive spine surgery (MISS), the challenges become more pronounced. Limited surgical access can make it difficult to insert and manipulate traditional pedicle screw systems, and assembling the screw-rod construct through small incisions often requires complex instrumentation and increased operative time. Furthermore, current designs may not adequately accommodate variations in patient anatomy, bone quality, or surgical technique, leading to suboptimal construct performance.

Accordingly, there is a need for a pedicle screw systems that enhances ease of insertion, holds the saddle portion of the system in position while adjusting rod member connection, and otherwise provides more reliable and adaptable fixation, both for polyaxial and uniplanar installation. Such improvements should reduce surgical complexity, minimize the risk of complications, and maintain or improve the mechanical stability necessary for successful spinal fusion and patient recovery.

SUMMARY OF THE PRESENT INVENTION

The present invention provides a modular pedicle screw assembly for use in minimally invasive spine surgery. The assembly includes a pedicle screw shank having an insertion end for engagement with a vertebra and a connector end with a conical outer surface and an inner driver receptacle configured to receive a driver tool for rotational insertion. In a preferred embodiment, the shank defines a passageway adapted to receive a positioning wire to facilitate accurate placement. A spherical collet with compression slits is securable to the connector end, allowing the collet to be compressed for locking engagement. The collet has upper and lower openings to permit driver tool access. A split ring with a chamfered lower inner edge and an associated cap are positioned over the collet. A saddle is coupled to the collet, the saddle having a U-shaped channel for receiving a spinal rod and a threaded section for receiving a set screw. Tightening the set screw compresses the cap and split ring to lock the rod and saddle in place while allowing the collet to provide a polyaxial or uniplanar connection between the screw shank and the rod. This modular configuration facilitates insertion through minimal incisions, improves surgical access, and enables secure, adjustable fixation during spinal stabilization procedures.

An objective of the invention is to provide an improved polyaxial modular screw using a collet lockable to a connector end.

Another objective of the invention is to disclose a modular screw having a sleeve to prevent set screw expansion of the connector.

Yet another objective of the invention is to disclose the use of removable extension arms for ease of installation;

Yet still another objective of the invention is to disclose a uniplanar connector to limit rotation of a connector to a single plane.

Still another objective is to teach the use of a screw assembly wherein the screw shank diameter may be increased or decreased without affecting the saddle connection.

Other objectives and advantages of this invention will become apparent from description taken in the following conjunction with the accompanying drawings wherein are set forth, by way of illustration and example, certain embodiments of this invention. The drawings constitute a part of this specification, include exemplary embodiments of the present invention, and illustrate various objects and features thereof.

DETAILED DESCRIPTION OF THE INVENTION

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

Figure 1:
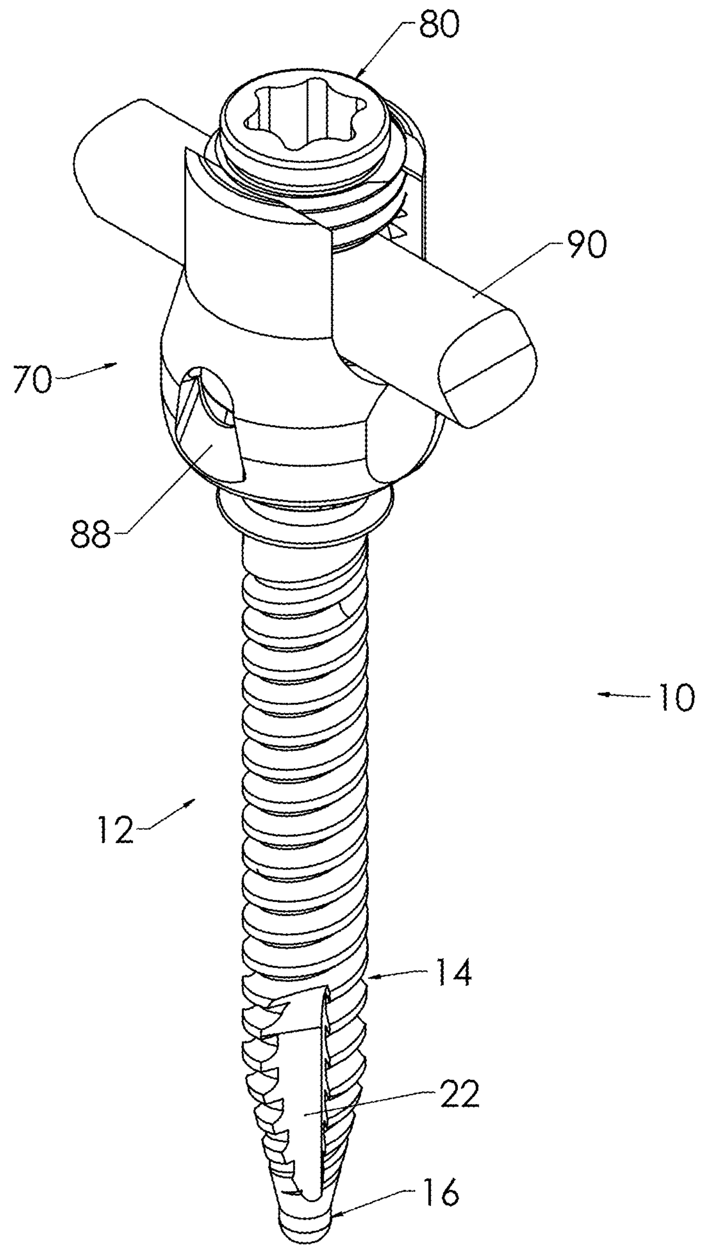
FIG. 1 is an upper perspective view of a modular screw.
Figure 2:
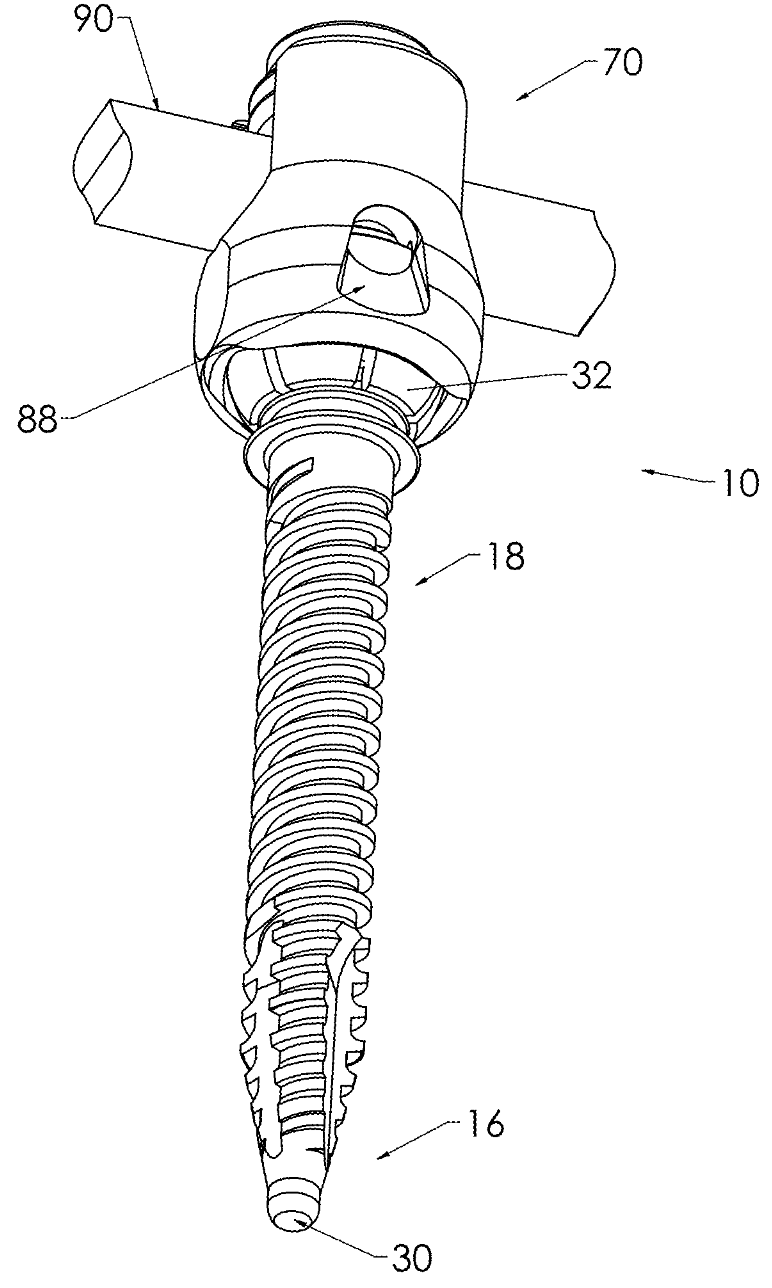
FIG. 2 is a lower perspective view thereof.
Figure 3:
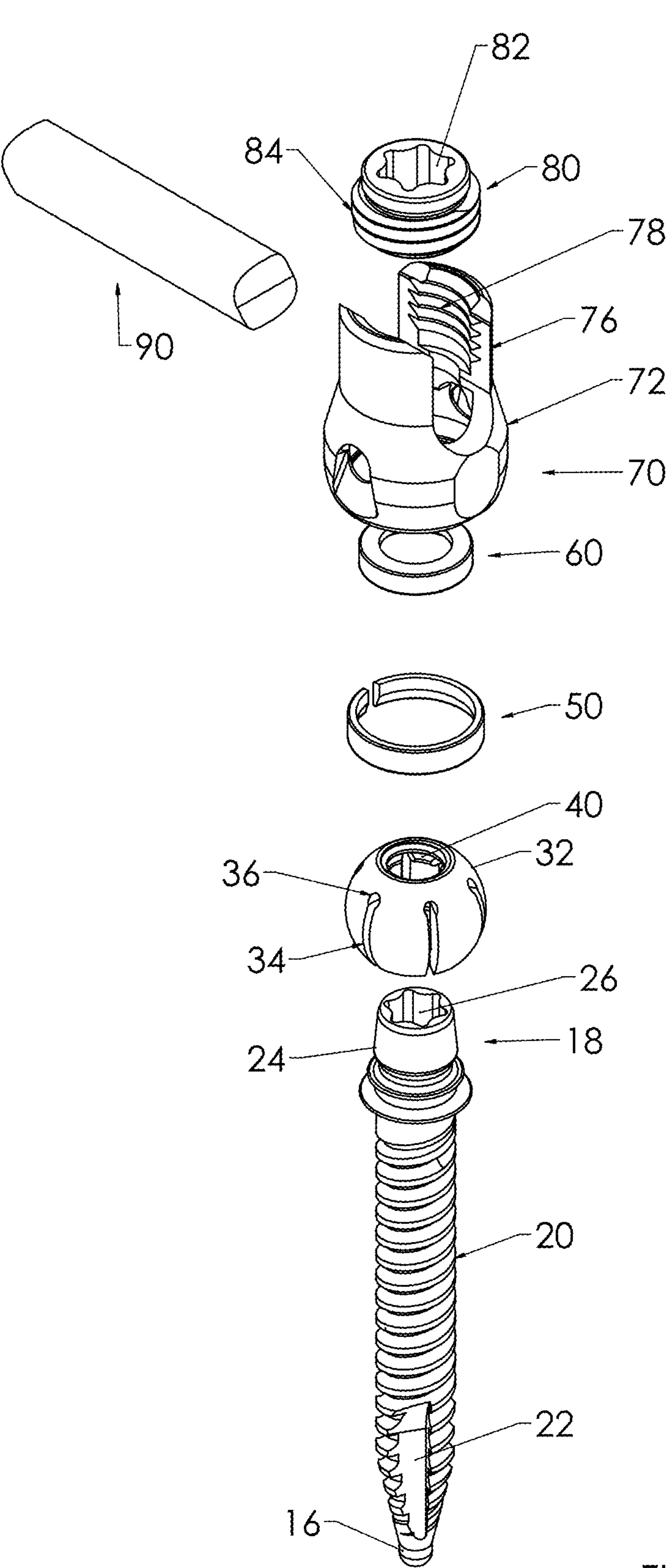
FIG. 3 is an upper perspective exploded view thereof.
Figure 4:
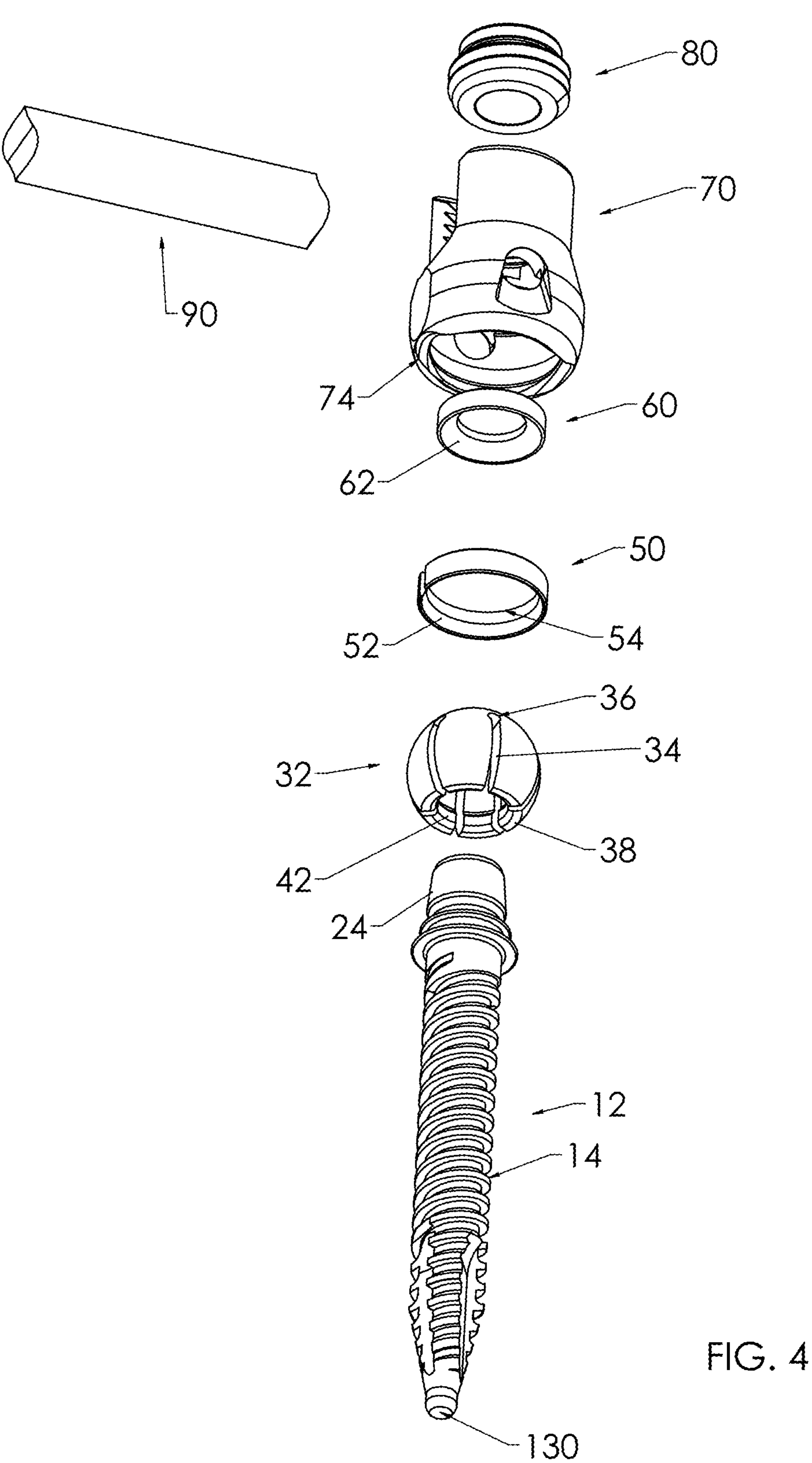
FIG. 4 is a lower perspective exploded view thereof.
Figures 5, 6:
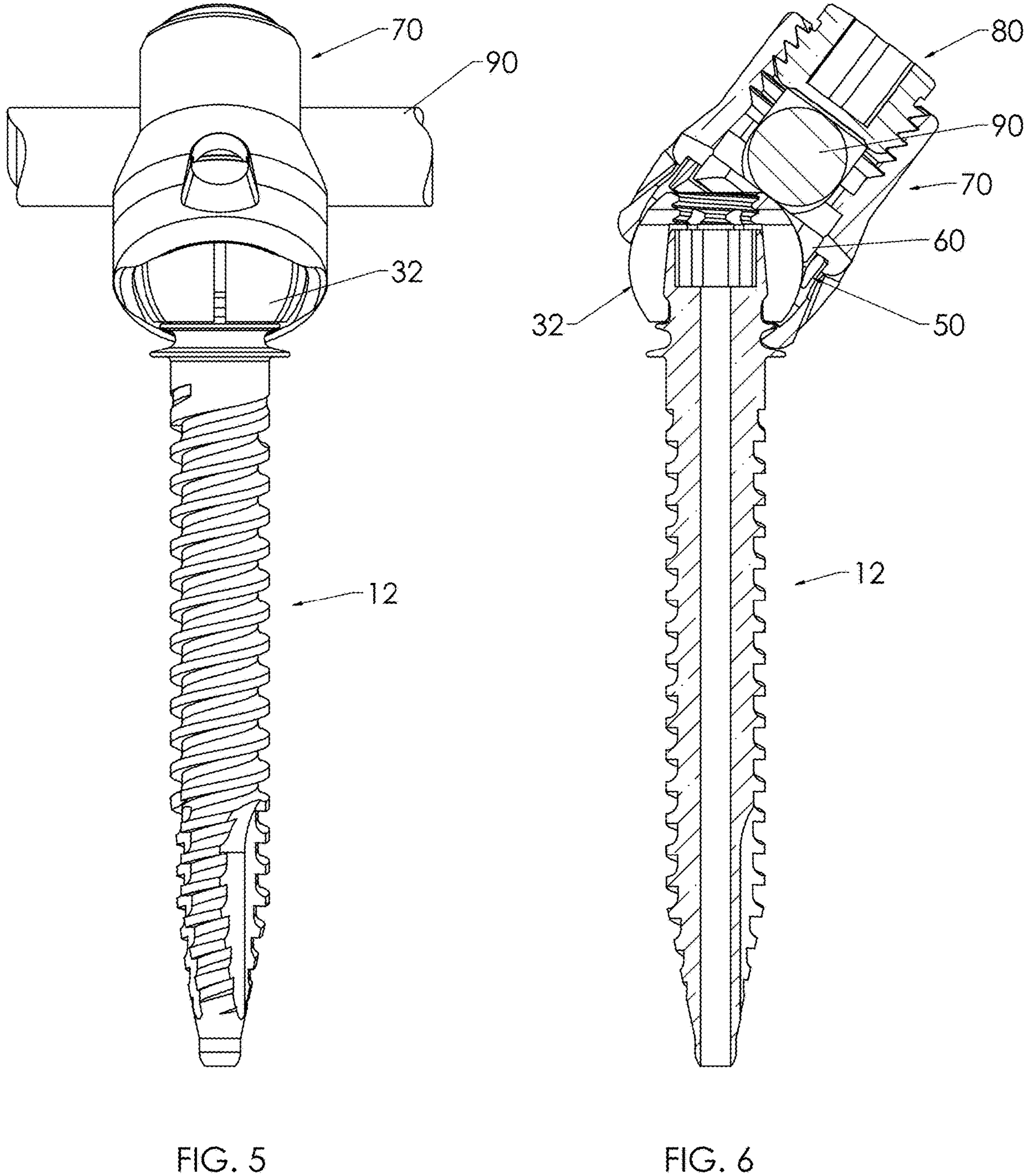
FIG. 5 is a front plane view thereof.
FIG. 6 is a cross section side view of FIG. 5.

Referring to FIGS. 1-6, a modular screw assembly 10 consists of a pedicle screw 12 formed from a shank 14 having an insertion end 16 and a connector end 18. The shank 14 having bone threads 20 graduating from the insertion end 16 to the connector end 18. The insertion end 16 may include a cut 22 to facilitate insertion into bone or spinal vertebrae. The connector end 18 having an outer surface 24 with a conical shape and an inner surface forming a driver receptacle 26.

The driver receptacle 26 is shaped for receipt of a driver tool allowing rotation of the shank. The driver receptacle 26 may be configured to accept a hexagonal socket, star drive, or other torque-transmitting interface that allows the shank 14 to be threaded to bone by rotation of the driver tool engaging the driver receptacle 26. In a preferred embodiment the shank includes a passageway 30 that can receive a positioning wire, not shown, for ease of shank placement.

A spherical shaped collet 32 is operatively associated with and securable to the connector end 18. The collet 32 having a plurality of compression slits 34 that extend from an upper portion 36 of the collet 32 through a lower edge 38 of the collet 32. The compression slits 34 allow the spherical ball 32 to be compressed around the connector end 24 for lockable securement. The collet 32 having an open upper passageway 40 extending to an open lower passageway 42, allowing insertion of a driver tool used to engage the receptacle 26.

A split ring 50 having a chamfered lower inner edge 52 is positioned over the collet 32 together with a cap 60 constructed and arranged to fit a tolerance opening 54 within the split ring 50. An inner surface 62 of the cap 60 conforming to the spherical shape of the collet 32.

A saddle 70 couples to the collet 32. The saddle 70 having a U-shaped opening 72 with a lower section 74 for receipt of a rod member 90 and a threaded upper section 76 for receipt of a set screw 80. The set screw having tool receptacle 82. Threads 84 engage the saddle threads 78. The threads 78 and 84 may consist of an interlocking thread to prevent splaying of the saddle when the screw 80 is tightened. The split ring 50, cap 60 and saddle 70 allow insertion of a driver tool to engage the driver receptacle 26.

The split ring 50 applying pressure to the collet 32 to keep the saddle in a stationary position while the rod member is being installed. The split ring 50 providing sufficient engagement with the collet to prevent the saddle from flopping over. Once the rod member has been positioned, the set screws is tightened which locks saddle to the collet by applying pressure to the cap 60. A rod member 90 is placed in the lower section 74 and used in compressing the cap 60 by tightening the set screw 80 to lock the rod member 90 and saddle 70 in a fixed position. The saddle includes indentations 88 to hold with a tool while the set screw 80 is being torque tightening. The collet 32 providing a polyaxial attachment between the shank 14 and rod member 90.

Figure 7:
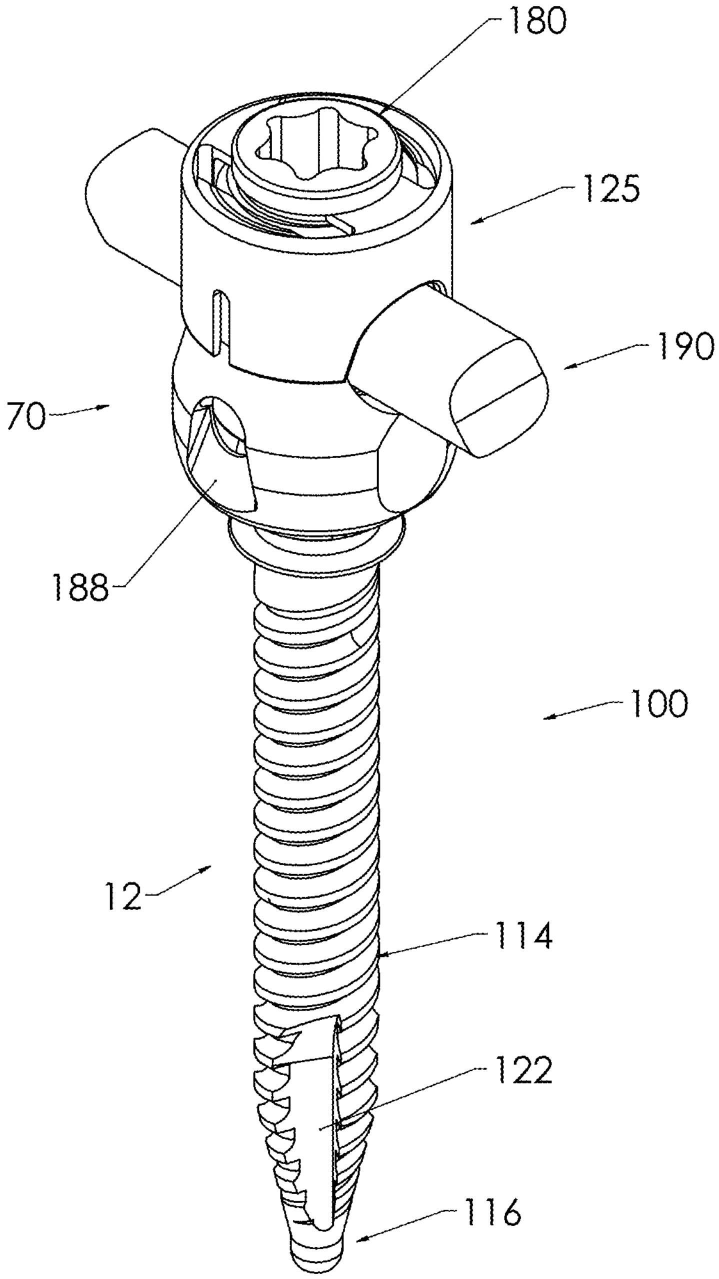
FIG. 7 is an upper perspective view of a sleeved screw.
Figure 8:
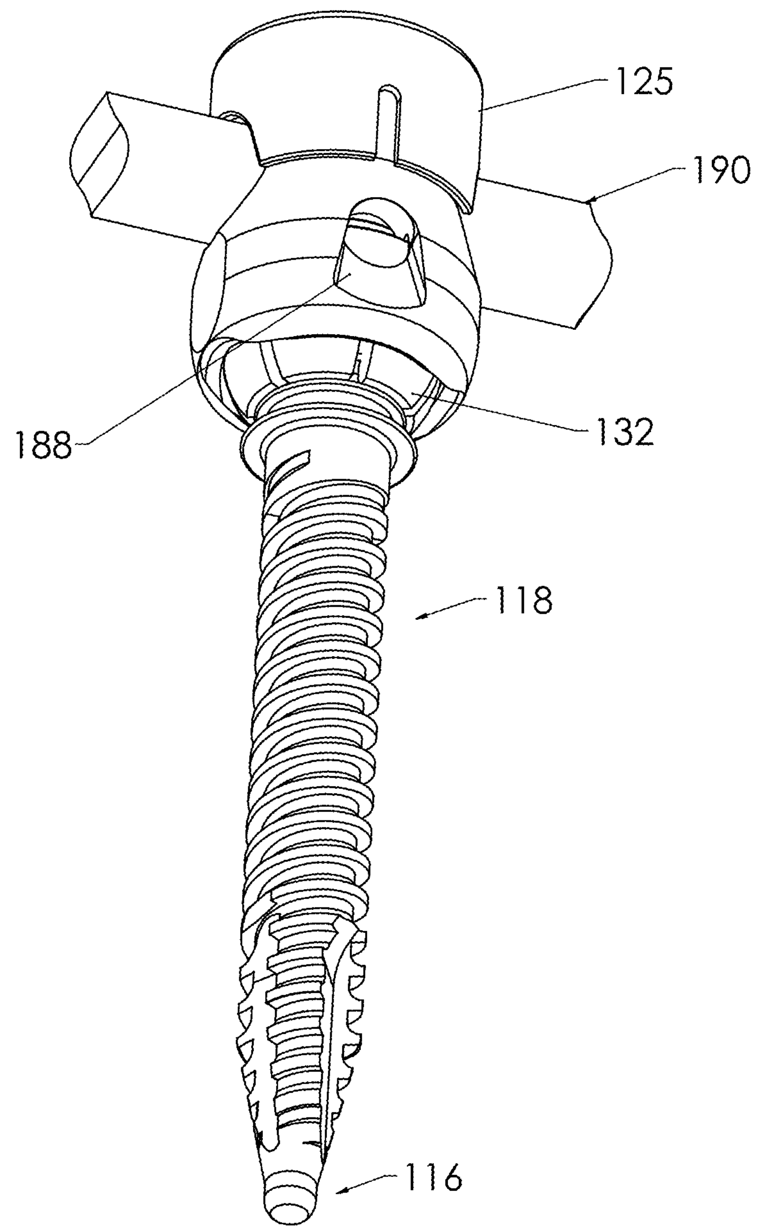
FIG. 8 is a lower perspective view thereof.
Figure 9:
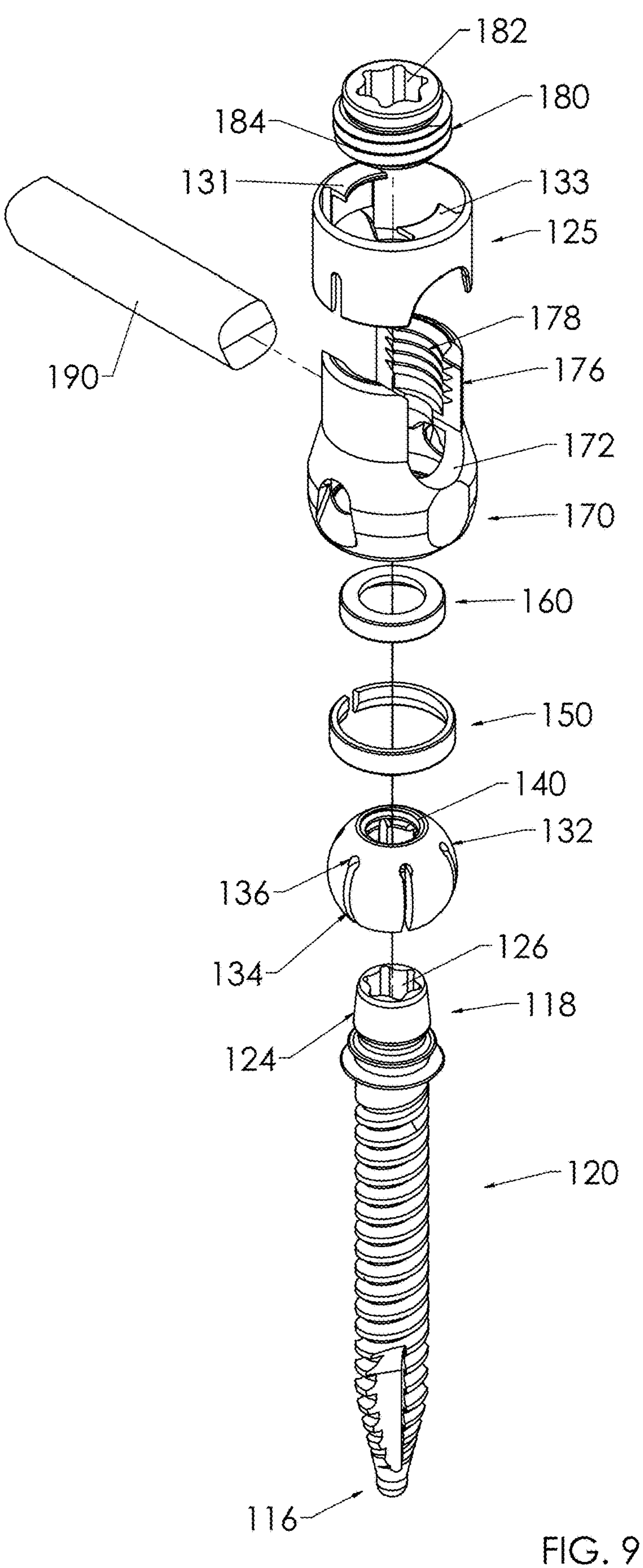
FIG. 9 is an upper perspective exploded view thereof.
Figure 10:
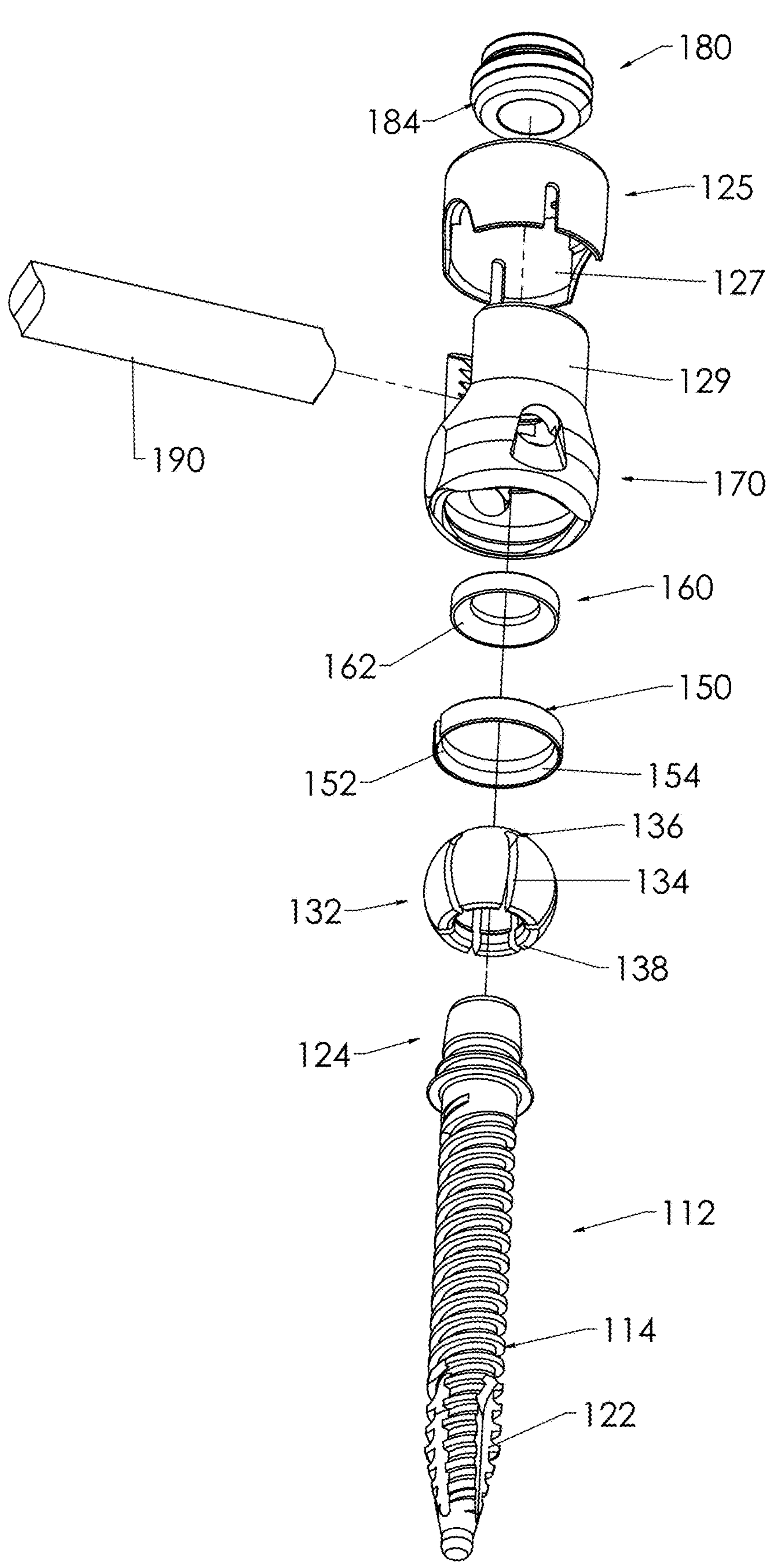
FIG. 10 is a lower perspective exploded view thereof.
Figure 11:
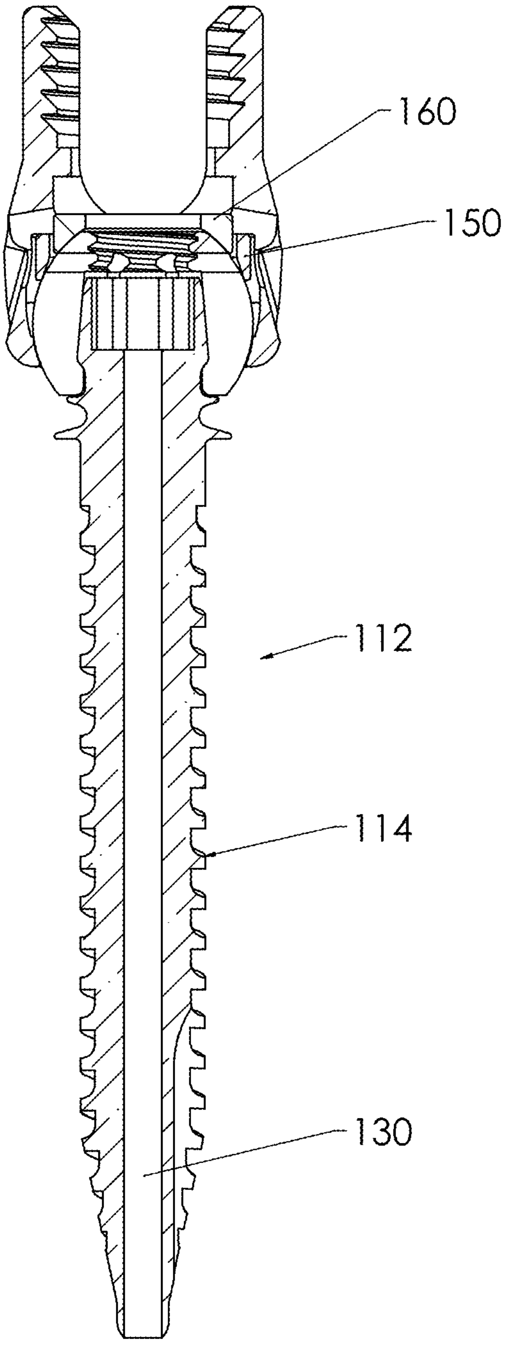
FIG. 11 is a cross sectional view without a set screw.
Figure 12:
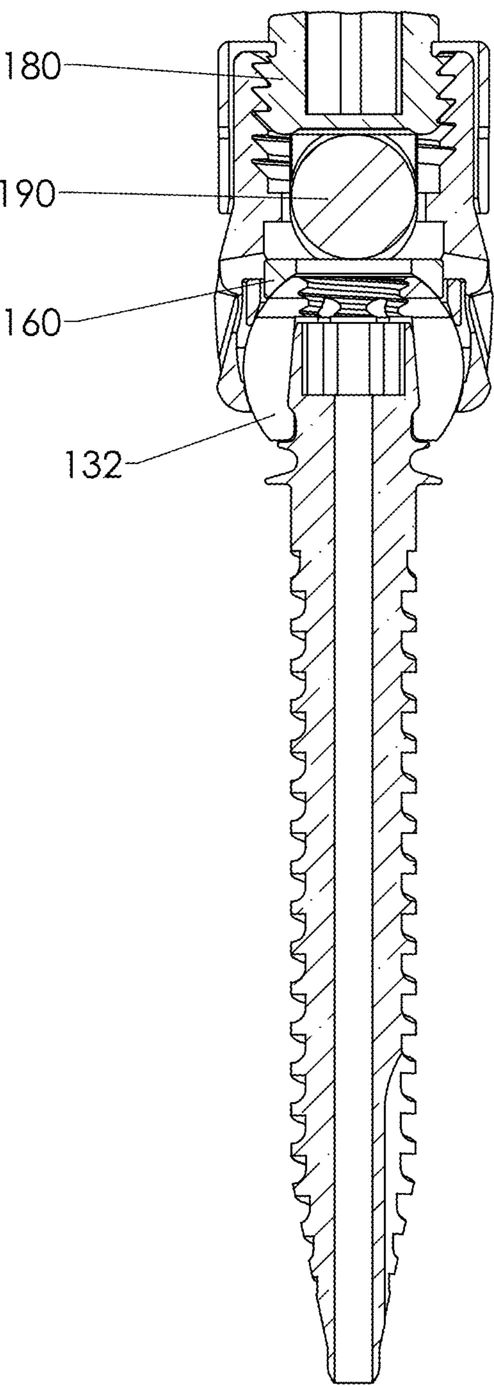
FIG. 12 is a cross sectional view with a set screw tightened.
Figures 13, 14:
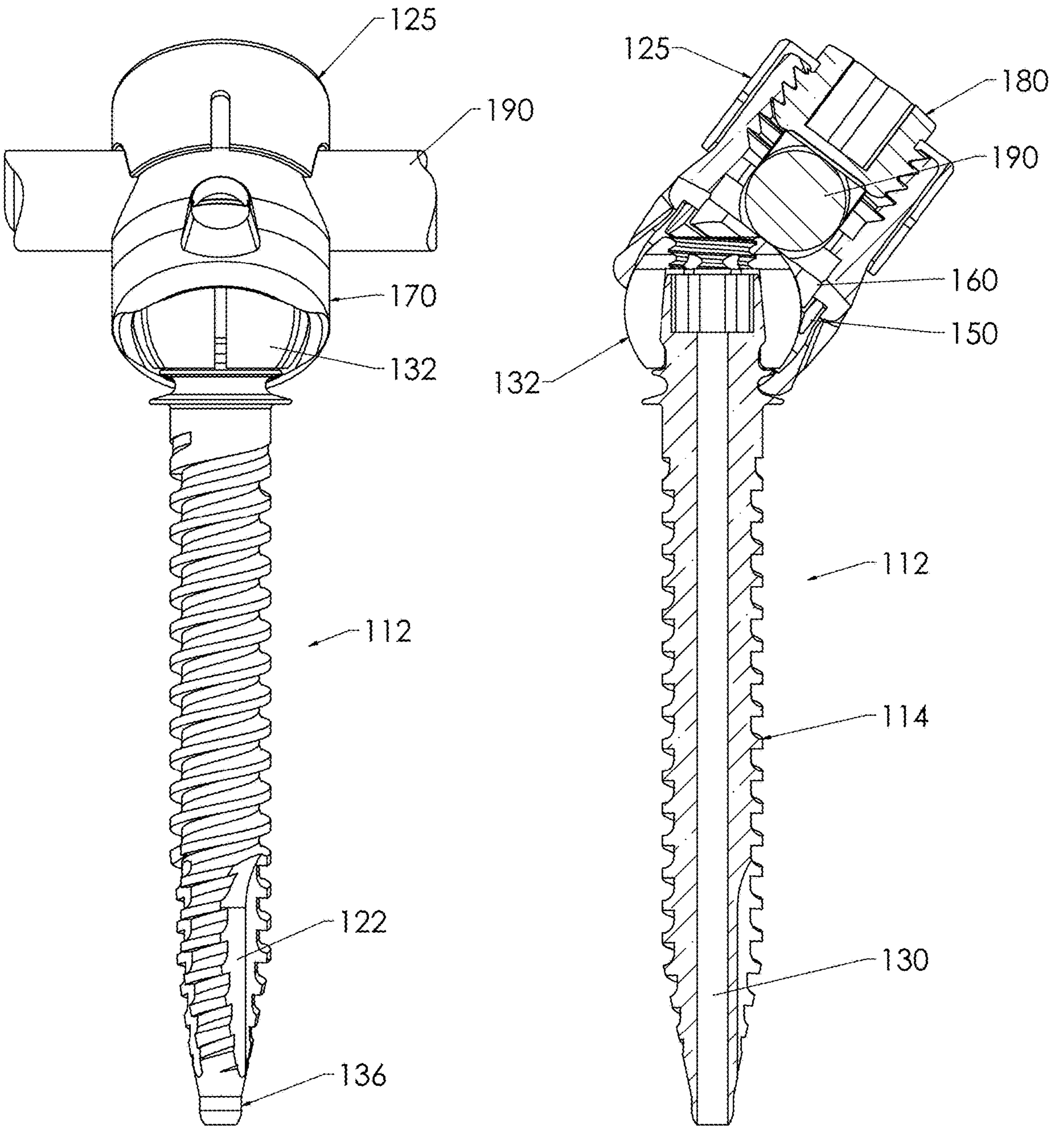
FIG. 13 is a front plane view thereof with an angled head.
FIG. 14 is a side plane view of FIG. 13.

Referring to FIGS. 7-14, illustrated is the modular screw assembly 100 with a sleeve 125. The pedicle screw 112 is formed from a shank 114 having an insertion end 116 and a connector end 118. The shank 114 having bone threads 120 graduating from the insertion end 116 to the connector end 118. The insertion end 116 may include a thread cut 122 to facilitate insertion into bone or spinal vertebrae. The connector end 118 having an outer surface 124 with a conical shape and an inner surface forming a driver receptacle 126.

The driver receptacle 126 is shaped for receipt of a driver tool allowing rotation of the shank. The driver receptacle 126 may be configured to accept a hexagonal socket, star drive, or other torque-transmitting interface that allows the shank 114 to be threaded to bone by rotation of the driver tool engaging the driver receptacle 126. In a preferred embodiment the shank includes a passageway 130 that can receive a positioning wire, not shown, for ease of shank placement.

A spherical shaped collet 132 is operatively associated with and securable to the connector end 118. The collet 132 having a plurality of compression slits 134 that extend from an upper portion 136 of the collet 132 through a lower edge 138 of the collet 132. The compression slits 134 allow the spherical ball 132 to be compressed around the connector end 124 for lockable securement. The collet 132 having an open upper passageway 140 extending to an open lower passageway 142, allowing insertion of a driver tool used to engage the receptacle 126.

A split ring 150 having a chamfered lower inner edge 152 is positioned over the collet 132 together with a cap 160 constructed and arranged to fit a tolerance opening 154 within the split ring 150. An inner surface 162 of the cap 160 conforming to the spherical shape of the collet 132.

A saddle 170 couples to the collet 132. The saddle 170 having a U-shaped opening 172 with a lower section 174 for receipt of a rod member 190 and a threaded upper section 176 for receipt of a set screw 180. The set screw having tool receptacle 182. Threads 184 engage the saddle threads 178. The threads 178 and 184 may consist of an interlocking thread to prevent splaying of the saddle when the screw 180 is tightened. The split ring 150, cap 160 and saddle 170 allow insertion of a driver tool to engage the driver receptacle 126.

The split ring 150 applying pressure to the collet 132 to keep the saddle in a stationary position while the rod member is being installed. The split ring 150 providing sufficient engagement with the collet to prevent the saddle from flopping over. Once the rod member has been positioned, the set screws is tightened which locks saddle to the collet by applying pressure to the cap 160. A rod member 190 is placed in the lower section 174 and used in compressing the cap 160. The sleeve 125 is placed over the saddle 170 having an inner side wall 127 that fits over the outer surface 129 of the saddle 170. Tabs 131 and 133 extend inwardly from the inner side wall 127 and fit within the U-shaped saddle 170 opening. By tightening the set screw 180, the sleeve further engages the rod member 190 for locking the saddle 170 in a fixed position relative to the collet 132. The sleeve prevents the saddle 170 from splaying should the set screw 180 be improperly torque tightened, or employs non-interlocking threads. The saddle includes indentations 188 to hold with a tool while the set screw 180 is being torque tightening. The collet 132 providing a polyaxial attachment between the shank 114 and rod member 190.

Figure 15:
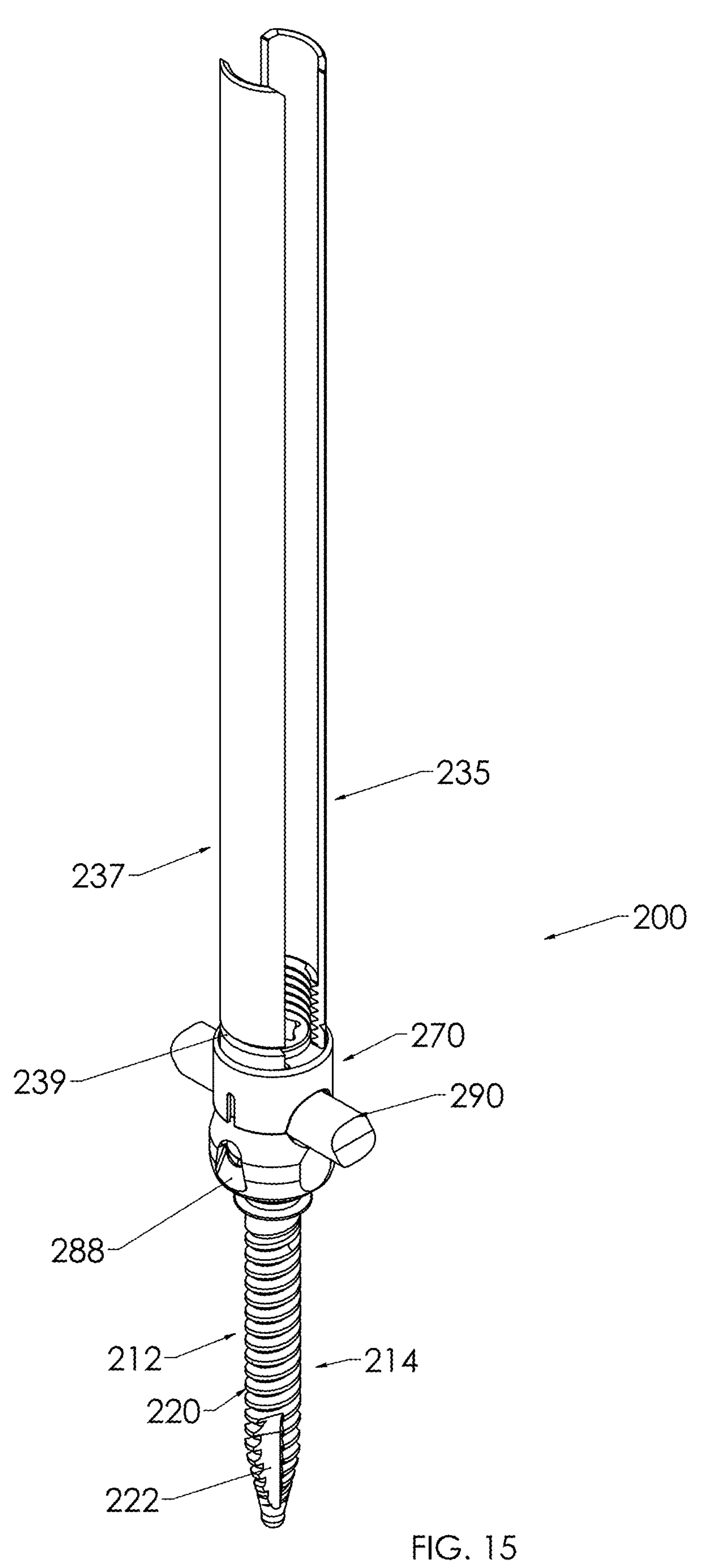
FIG. 15 is an upper perspective view of an extension sleeve.
Figure 16:
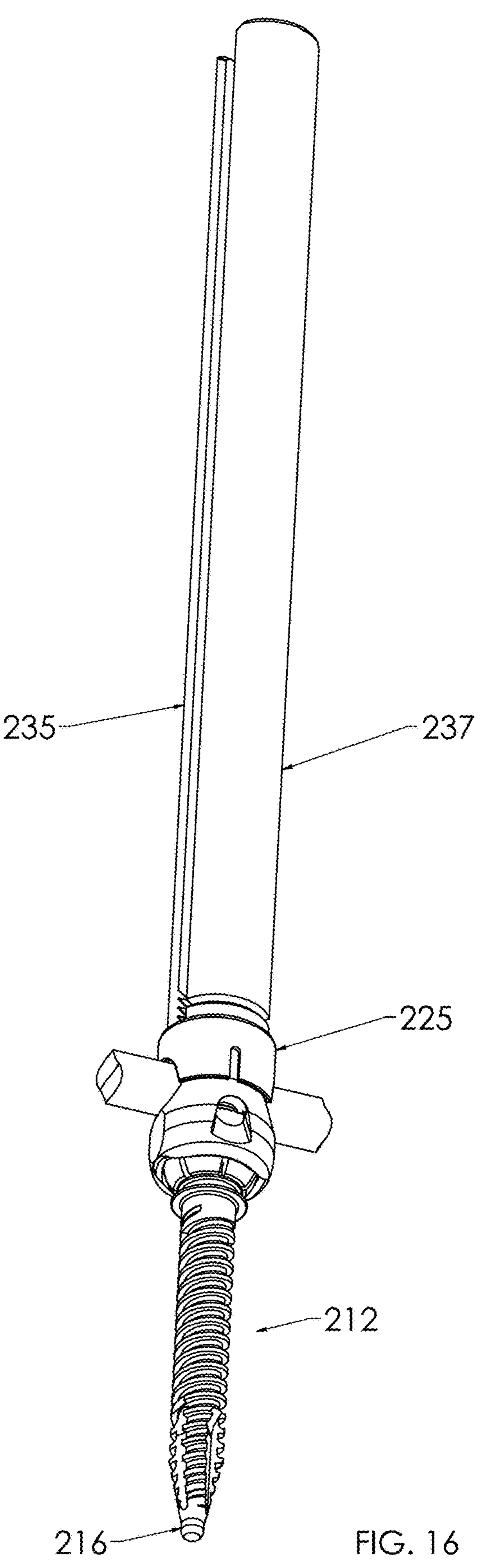
FIG. 16 is a lower perspective view thereof.
Figure 17:
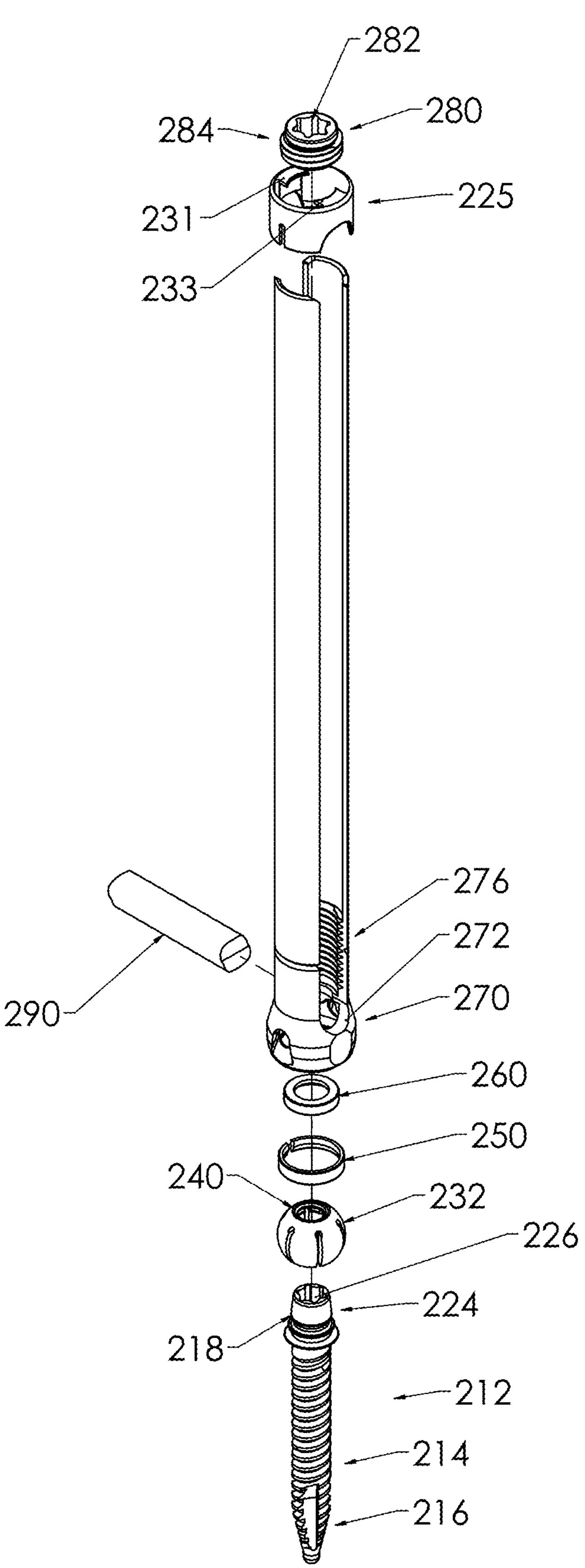
FIG. 17 is an upper perspective exploded front view thereof.
Figure 18:
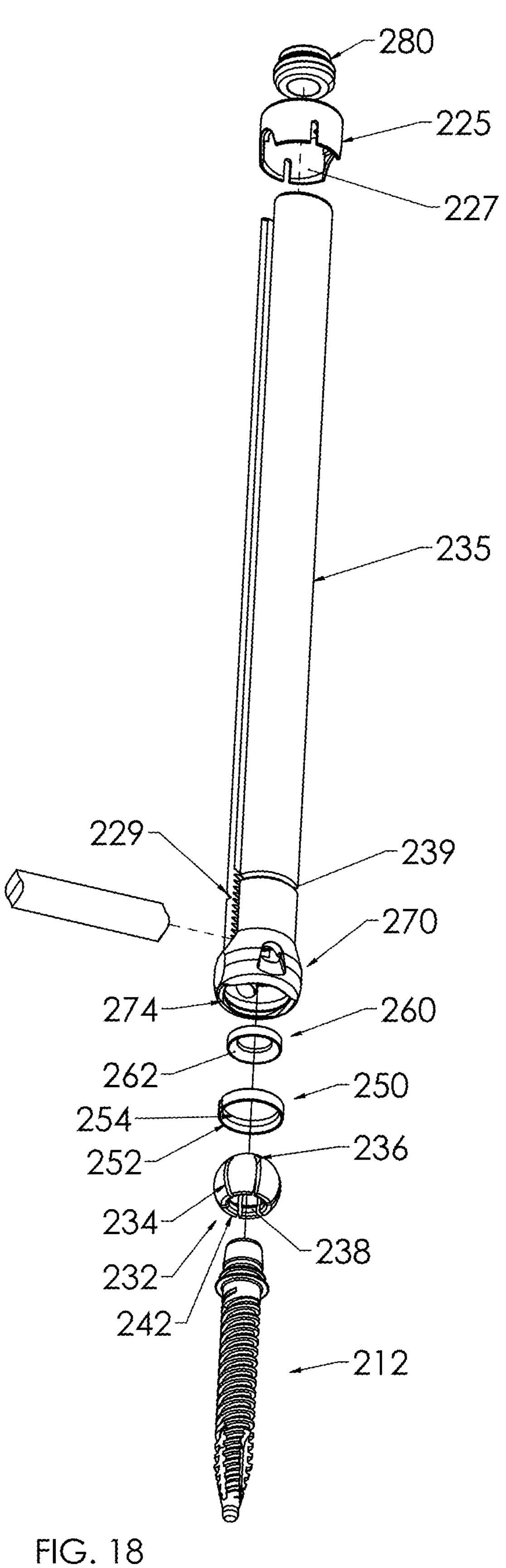
FIG. 18 is a lower perspective exploded rear view thereof.
Figures 19, 20:
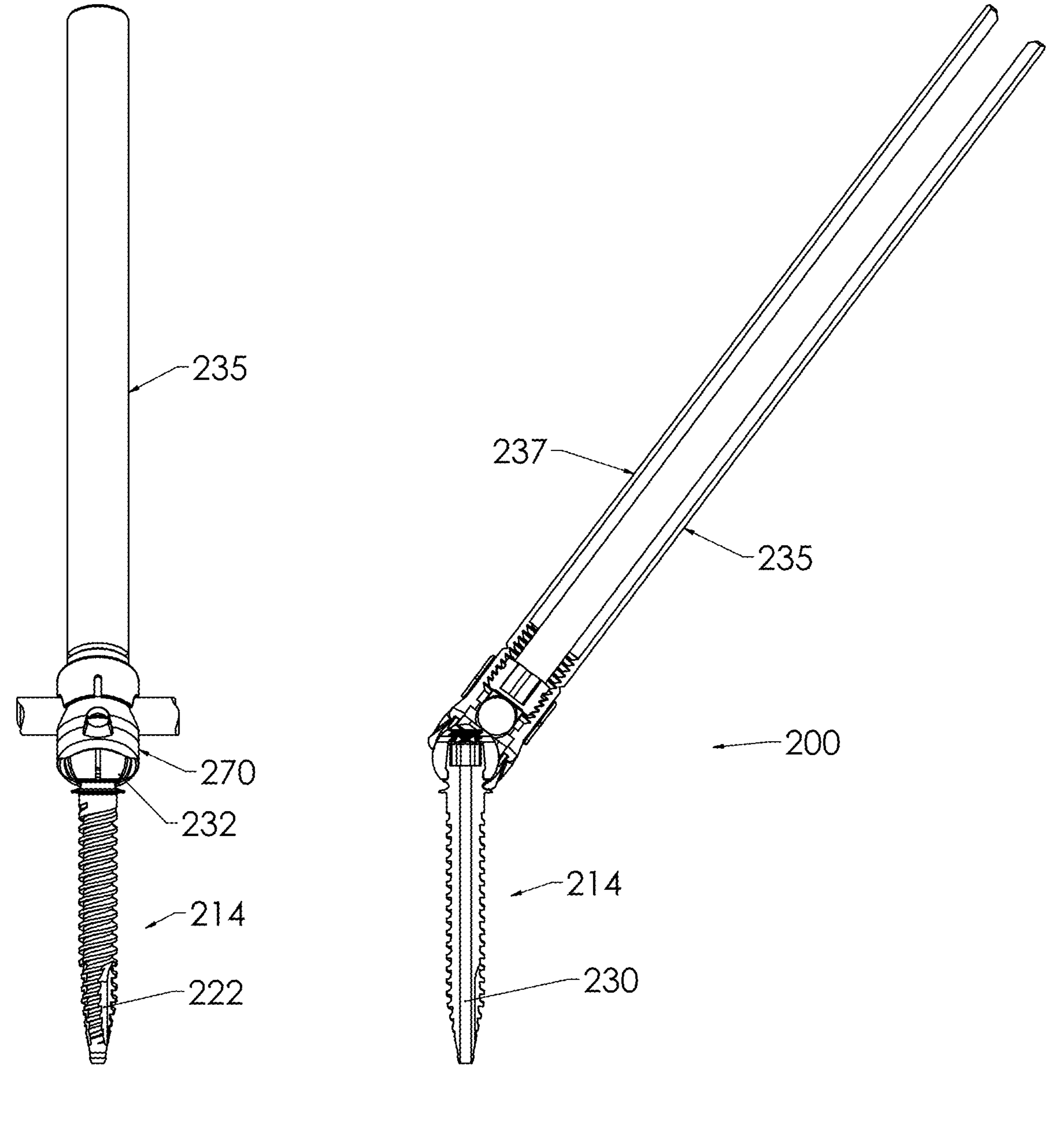
FIG. 19 is a front plane view thereof with an angled head.
FIG. 20 is a cross section side view of FIG. 19.

Referring now to FIGS. 15-20, illustrated is the modular screw assembly 200 with a sleeve 225 and extensions 235, 237. The pedicle screw 212 is formed from a shank 214 having an insertion end 216 and a connector end 218. The shank 214 having bone threads 220 graduating from the insertion end 216 to the connector end 218. The insertion end 216 may include a thread cut 222 to facilitate insertion into bone or spinal vertebrae. The connector end 218 having an outer surface 224 with a conical shape and an inner surface forming a driver receptacle 226.

The driver receptacle 226 is shaped for receipt of a driver tool allowing rotation of the shank. The driver receptacle 226 may be configured to accept a hexagonal socket, star drive, or other torque-transmitting interface that allows the shank 214 to be threaded to bone by rotation of the driver tool engaging the driver receptacle 226. In a preferred embodiment the shank includes a passageway 230 that can receive a positioning wire, not shown, for ease of shank placement.

A spherical shaped collet 232 is operatively associated with and securable to the connector end 218. The collet 232 having a plurality of compression slits 234 that extend from an upper portion 236 of the collet 232 through a lower edge 238 of the collet 232. The compression slits 234 allow the spherical ball 232 to be compressed around the connector end 224 for lockable securement. The collet 232 having an open upper passageway 240 extending to an open lower passageway 242, allowing insertion of a driver tool used to engage the receptacle 226.

A split ring 250 having a chamfered lower inner edge 252 is positioned over the collet 232 together with a cap 260 constructed and arranged to fit a tolerance opening 254 within the split ring 250. An inner surface 262 of the cap 260 conforming to the spherical shape of the collet 232.

A saddle 270 couples to the collet 232. The saddle 270 having a U-shaped opening 272 with a lower section 274 for receipt of a rod member 290 and a threaded upper section 276 for receipt of a set screw 280. The set screw 280 having tool receptacle 282. Threads 284 engage the saddle threads 278. The threads 278 and 284 may consist of an interlocking thread to prevent splaying of the saddle when the set screw 280 is tightened. The split ring 250, cap 260 and saddle 270 allow insertion of a driver tool to engage the driver receptacle 226.

The split ring 250 applying pressure to the collet 232 to keep the saddle in a stationary position while the rod member is being installed. The split ring 250 providing sufficient engagement with the collet to prevent the saddle from flopping over. Once the rod member has been positioned, the set screw 280 is tightened which locks saddle 270 to the collet 232 by applying pressure to the cap 260. A rod member 290 is placed in the lower section 274 and used in compressing the cap 260.

A sleeve 225 is placed over the saddle 270 having an inner side wall 227 that fits over the outer surface 229 of the saddle 270. Tabs 231 and 233 extend inwardly from the inner side wall 227 and fit within the U-shaped saddle 270. By tightening the set screw 280, the sleeve further engages the rod member 290 for locking the saddle 270 in a fixed position relative to the collet 232. The sleeve prevents the saddle 270 from splaying should the set screw 280 be improperly torque tightened, or employs non-interlocking threads. The saddle includes indentations 288 to hold with a tool while the set screw 280 is being torque tightening. The collet 232 providing a polyaxial attachment between the shank 214 and rod member 290. Once installed, extensions 235, 237 can be removed by moving toward the score line 239.

Figure 21:
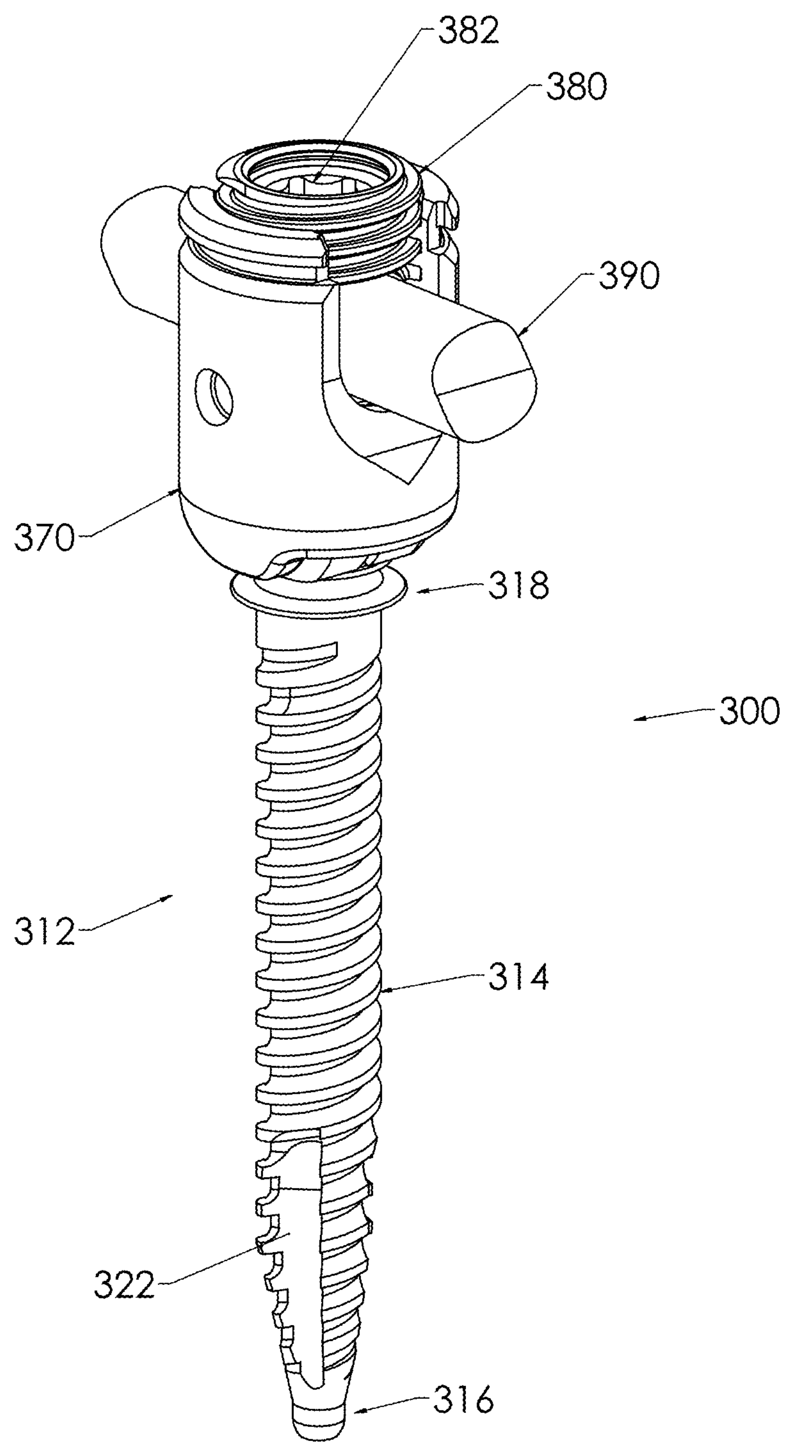
FIG. 21 is an upper perspective view of a uniplanar screw.
Figure 22:
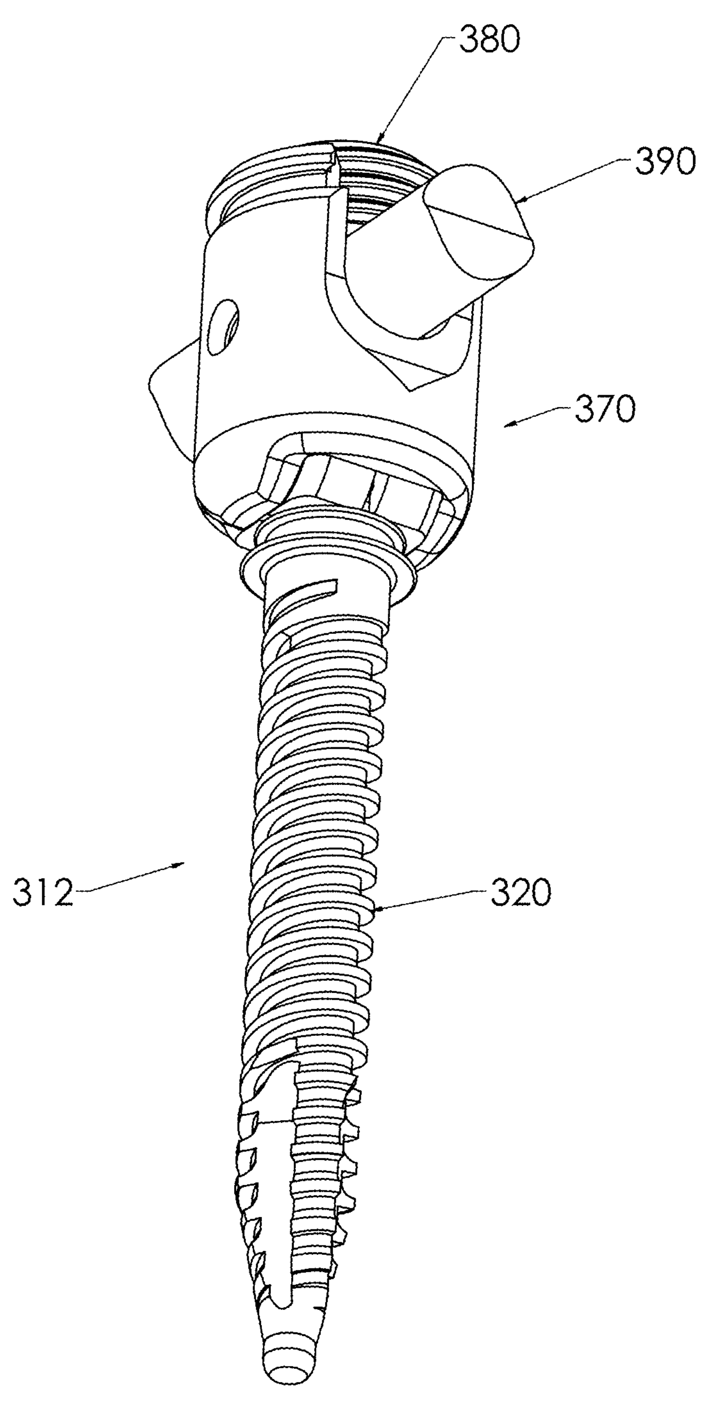
FIG. 22 is a lower perspective view thereof.
Figure 23:
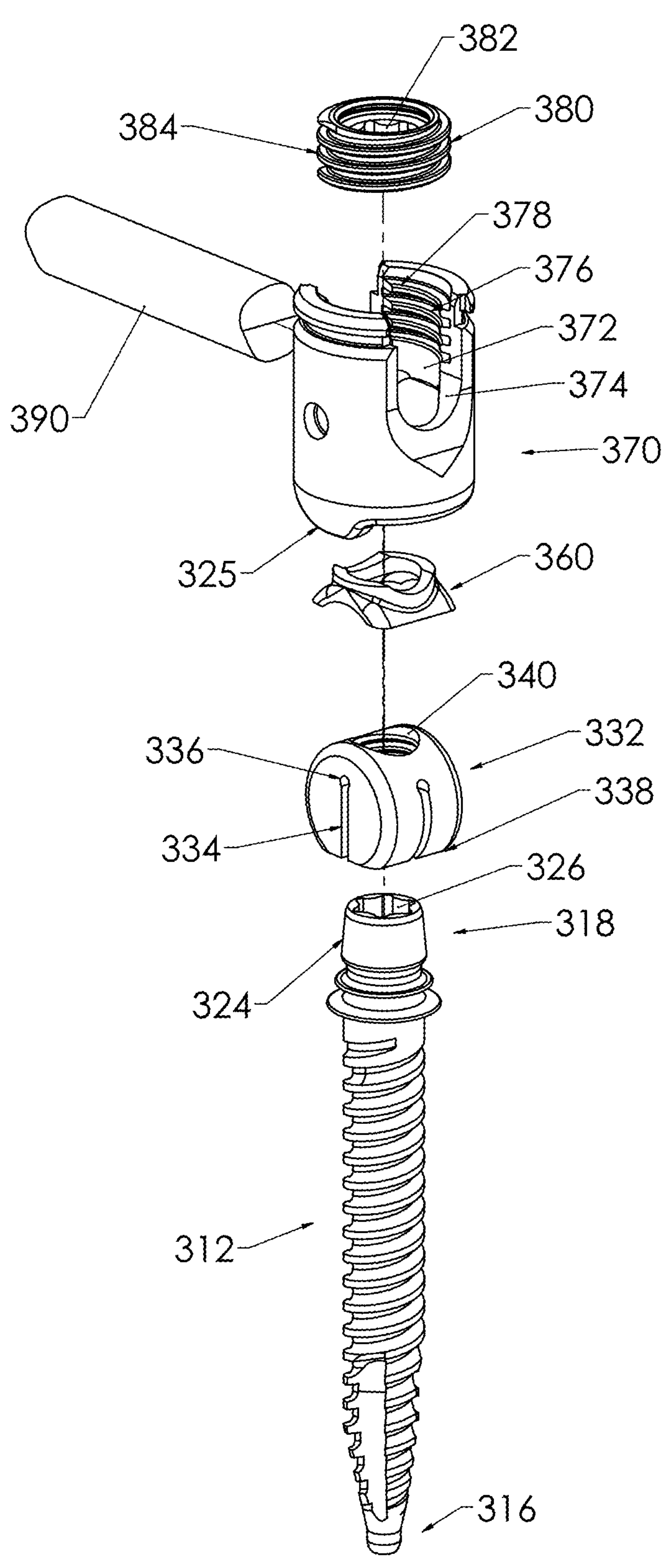
FIG. 23 is an upper perspective exploded front view thereof.
Figure 24:
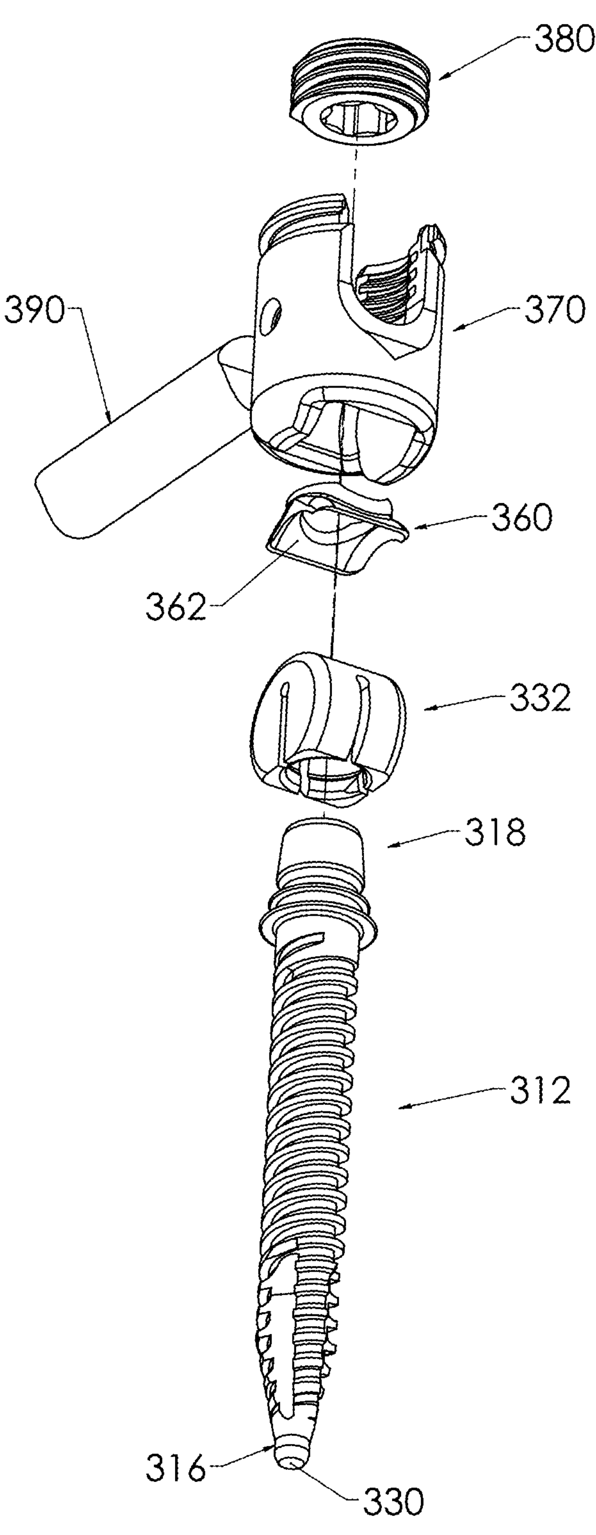
FIG. 24 is an lower perspective exploded rear view thereof.
Figures 25, 26:
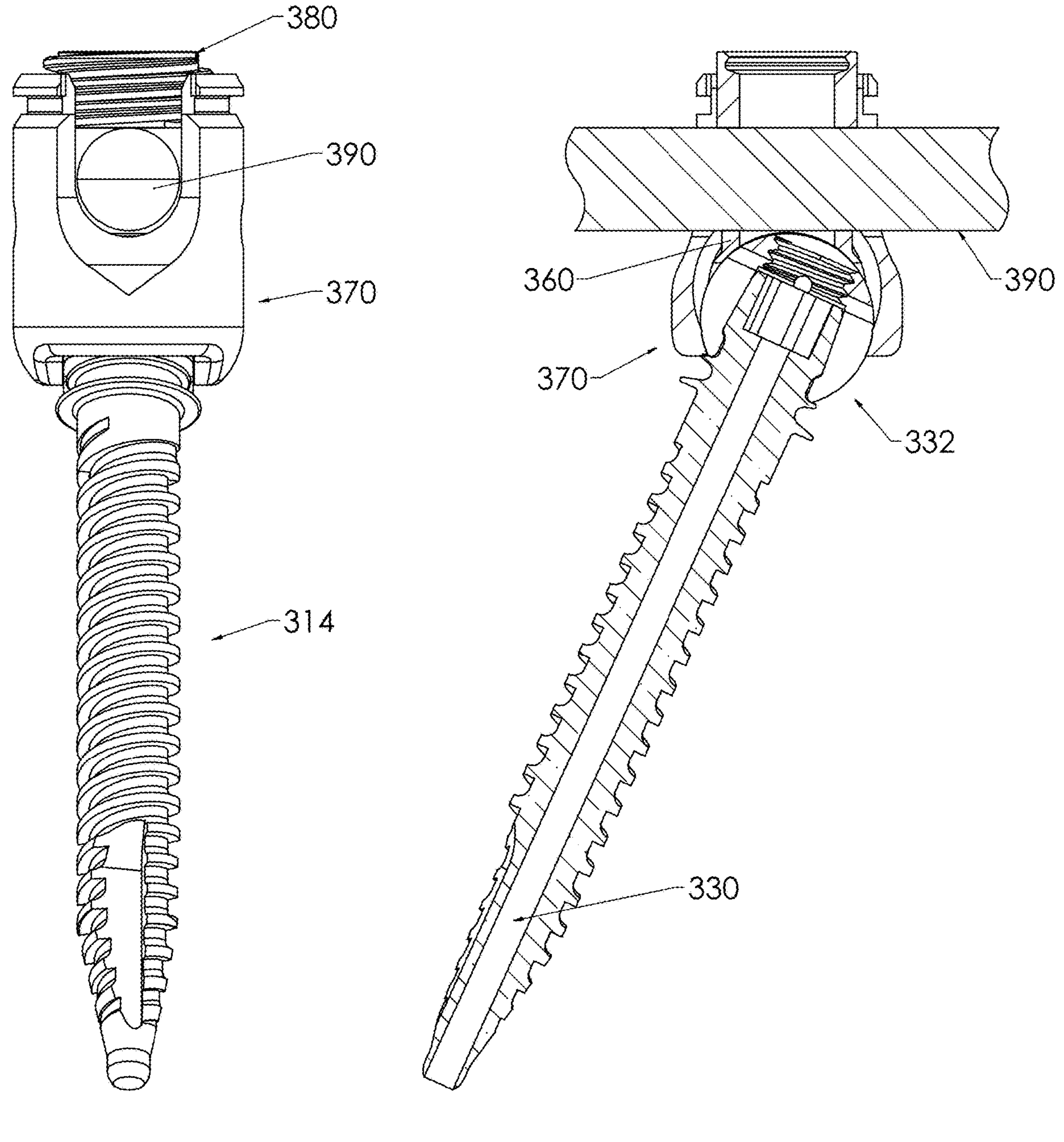
FIG. 25 is a front plane view thereof with the angle head.
FIG. 26 is a cross section side view of FIG. 25.

Referring now to FIGS. 21-26, illustrated is the modular screw assembly 300 in a uniplanar embodiment. The pedicle screw 312 is formed from a shank 314 having an insertion end 316 and a connector end 318. The shank 314 having bone threads 320 graduating from the insertion end 316 to the connector end 318. The insertion end 316 may include a thread cut 322 to facilitate insertion into bone or spinal vertebrae. The connector end 318 having an outer surface 324 with a conical shape and an inner surface forming a driver receptacle 326.

The driver receptacle 326 is shaped for receipt of a driver tool allowing rotation of the shank. The driver receptacle 326 may be configured to accept a hexagonal socket, star drive, or other torque-transmitting interface that allows the shank 314 to be threaded to bone by rotation of the driver tool engaging the driver receptacle 326. In a preferred embodiment the shank includes a passageway 330 that can receive a positioning wire, not shown, for ease of shank placement.

A uniplanar shaped collet 332 is operatively associated with and securable to the connector end 318. The collet 332 having a plurality of compression slits 334 that extend from an upper portion 336 of the collet 332 through a lower edge 338 of the collet 332. The compression slits 334 allow the collet 332 to be compressed around the connector end 324 for lockable securement. The collet 332 having an open upper passageway 340 allowing insertion of a driver tool used to engage the receptacle 326. A cap 360 having an inner surface 362 conforming to the shape of the collet 332.

A saddle 370 couples to the collet 332. The saddle 370 having a U-shaped opening 372 with a lower section 374 for receipt of a rod member 390 and a threaded upper section 376 for receipt of a set screw 380. The set screw 380 having tool receptacle 382. Threads 384 engage the saddle threads 378. The threads 378 and 384 may consist of an interlocking thread to prevent splaying of the saddle when the set screw 380 is tightened.

Once the rod member 390 has been positioned, the set screw 380 is tightened which locks saddle 370 to the collet 332 by applying pressure to the cap 360. A rod member 390 is placed in the lower section 374 and used in compressing the cap 360. The bottom edge 325 of the saddle 370 having assures the uniplanar rotation of the saddle 370 in respect to the collet. The collet 332 providing a unidirectional rotation with the shank 314.

Figure 27:
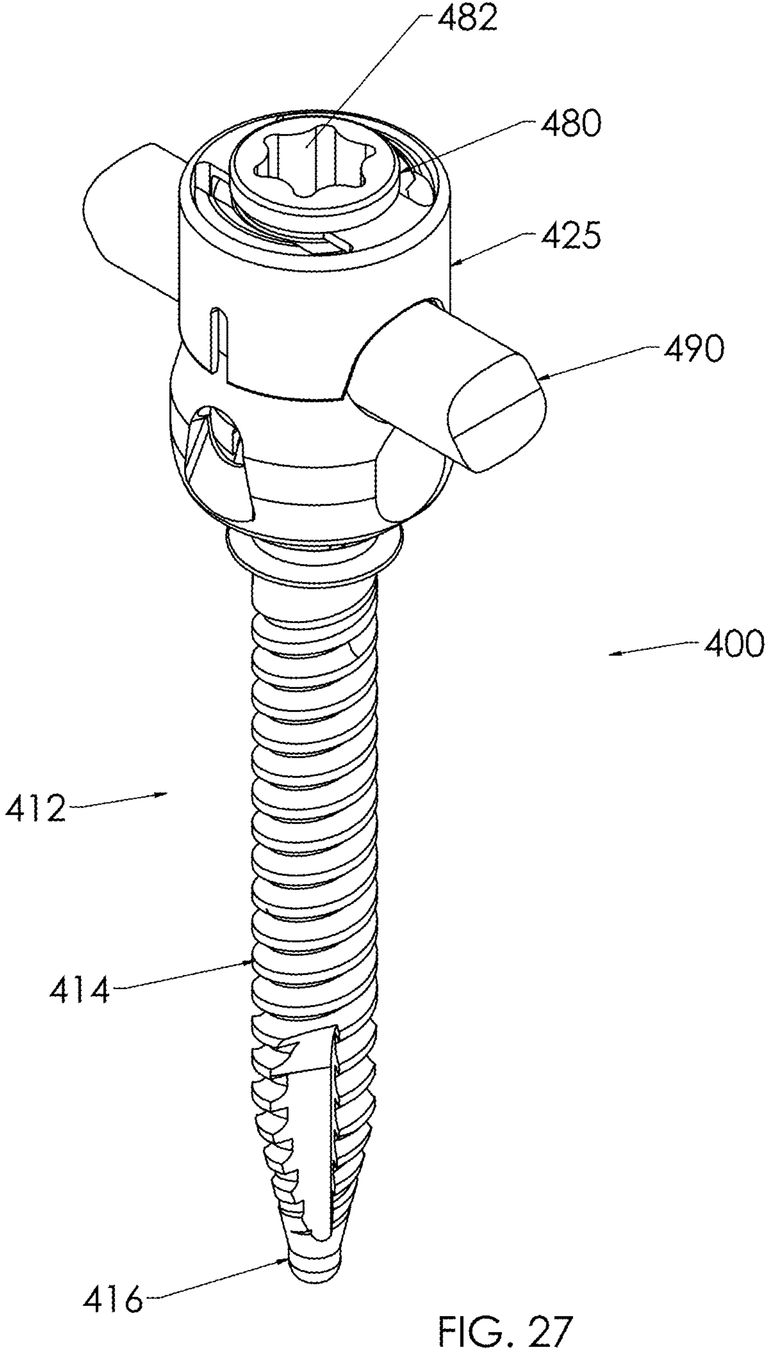
FIG. 27 is upper perspective view of a screw retention clip.
Figure 28:
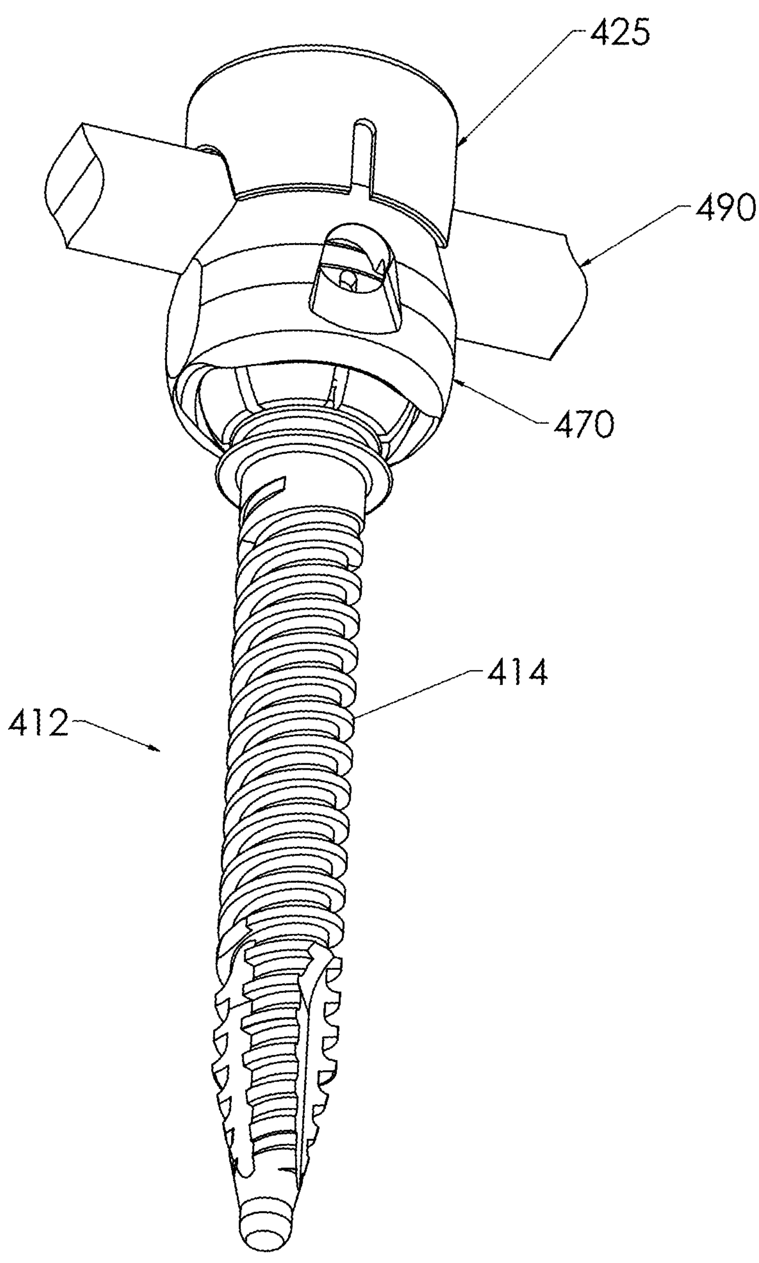
FIG. 28 is a lower perspective view thereof.
Figure 29:
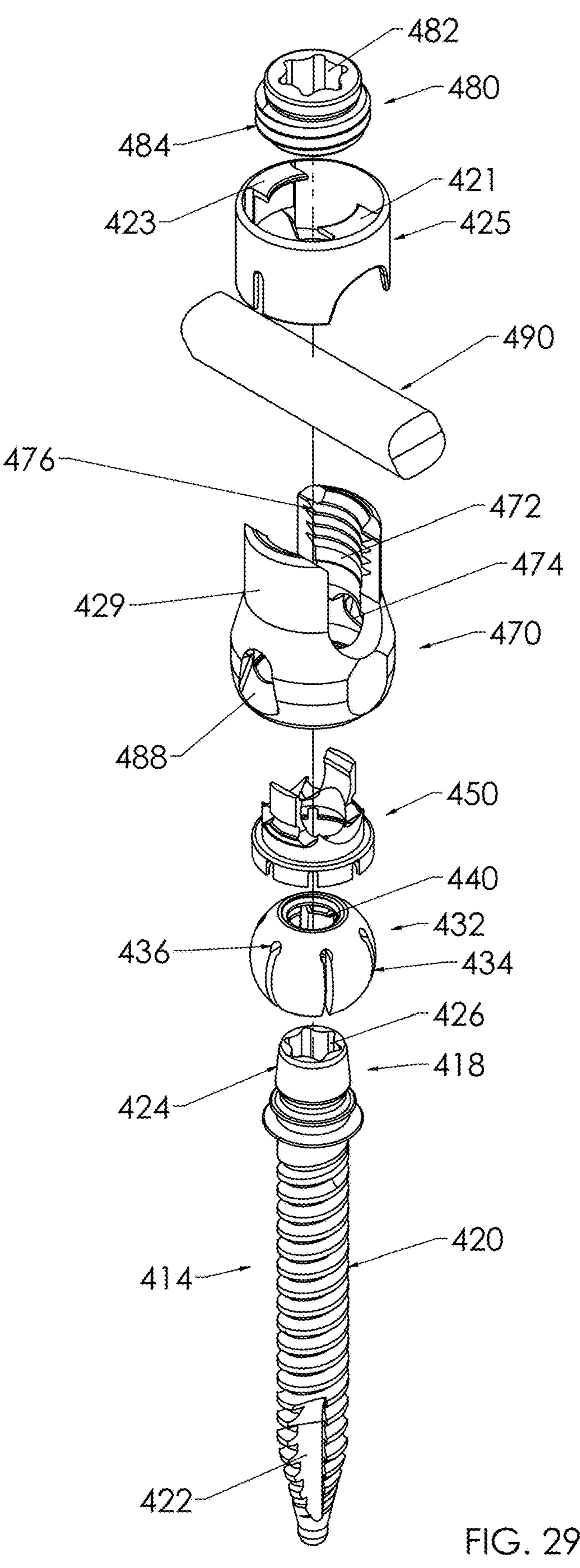
FIG. 29 is an upper perspective exploded front view thereof.
Figure 30:
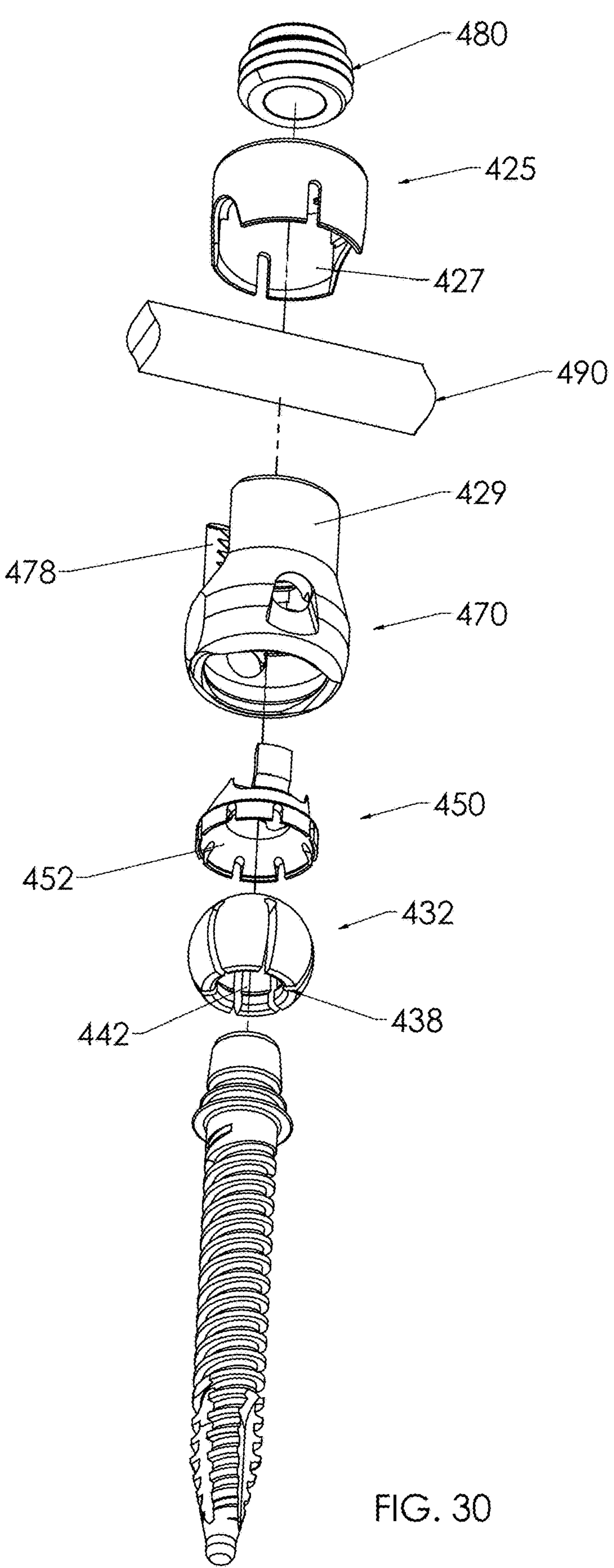
FIG. 30 is a lower perspective exploded rear view thereof.
Figure 31:
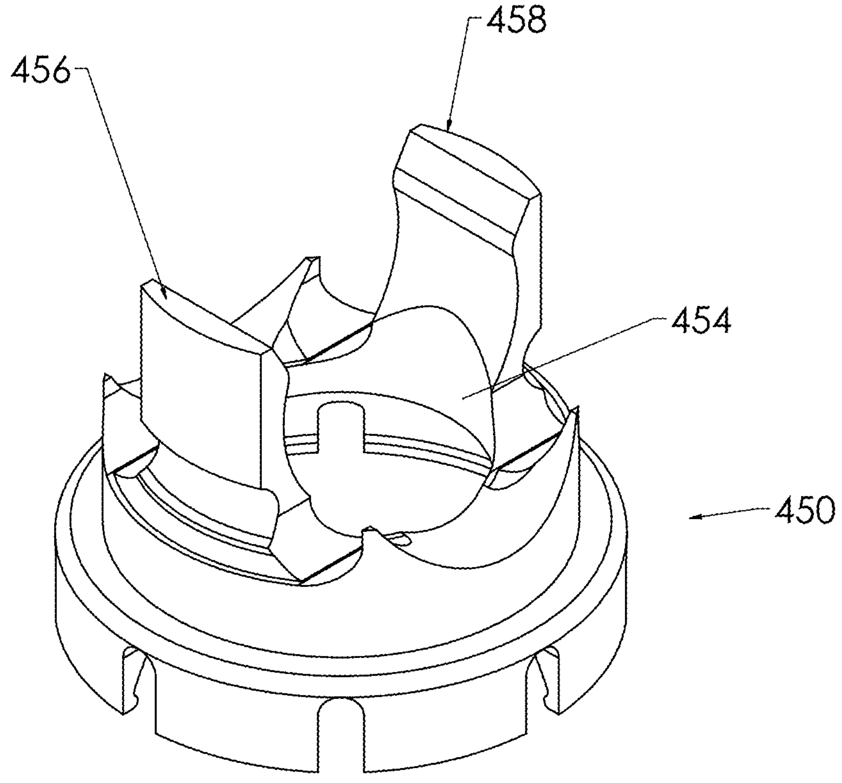
FIG. 31 is an upper perspective view of the retention clip.
Figure 32:
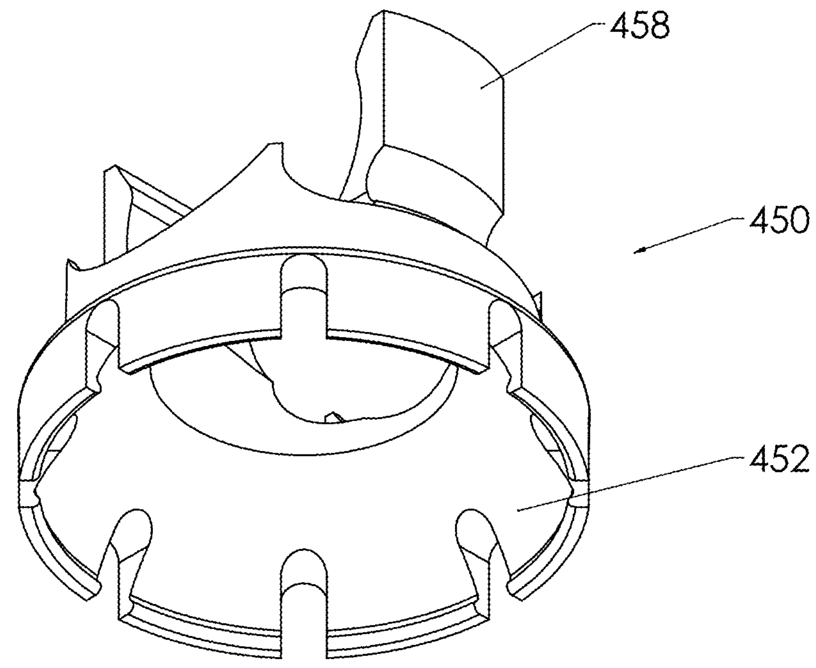
FIG. 32 is a lower perspective view of the retention clip.
Figures 33, 34A, 34B:
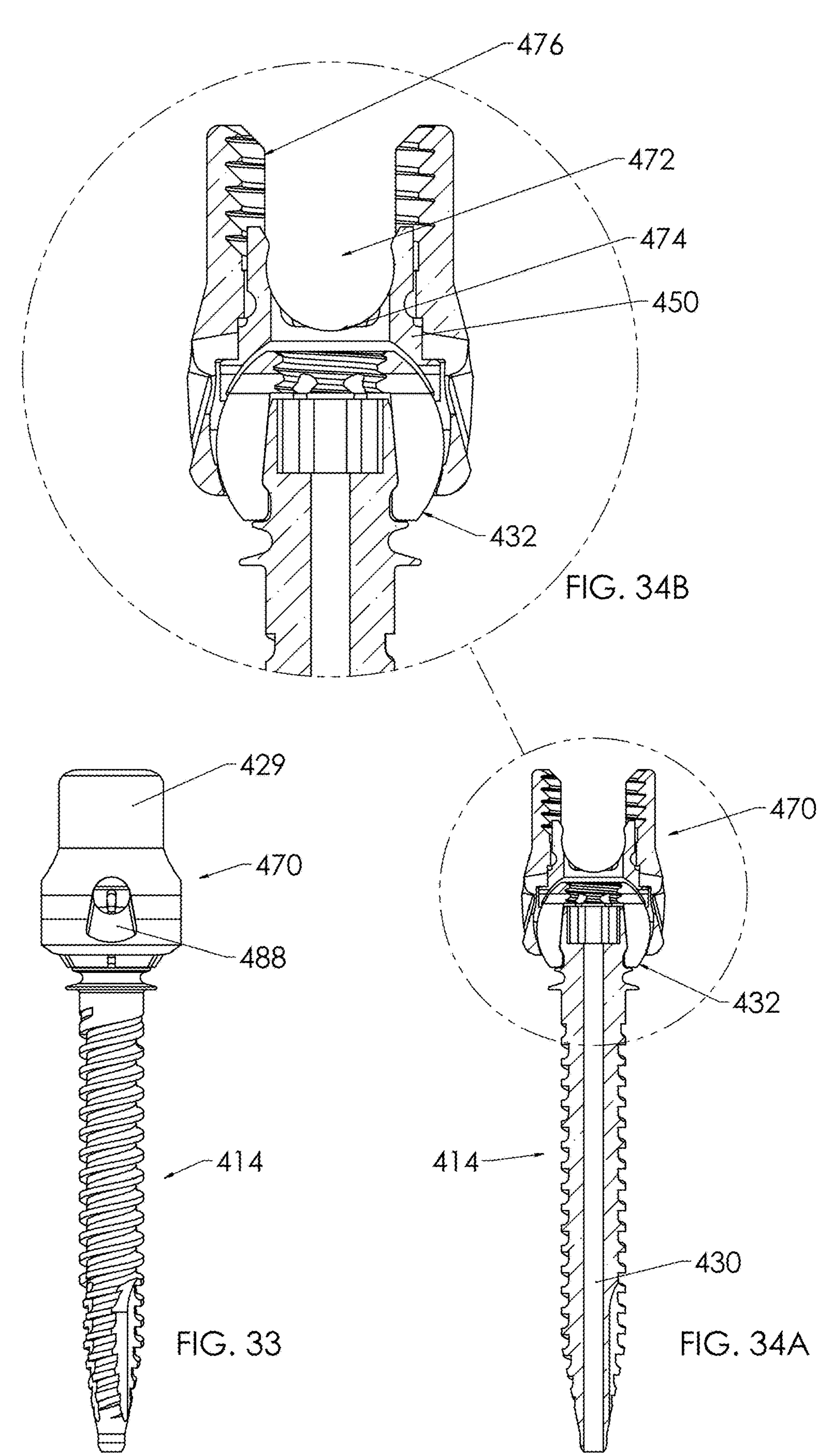
FIG. 33 is a front plane view of the retention clip screw.
FIG. 34A is a cross sectional view thereof.
FIG. 34B is a sectional view of FIG. 34A.
Figures 35, 36A, 36B:
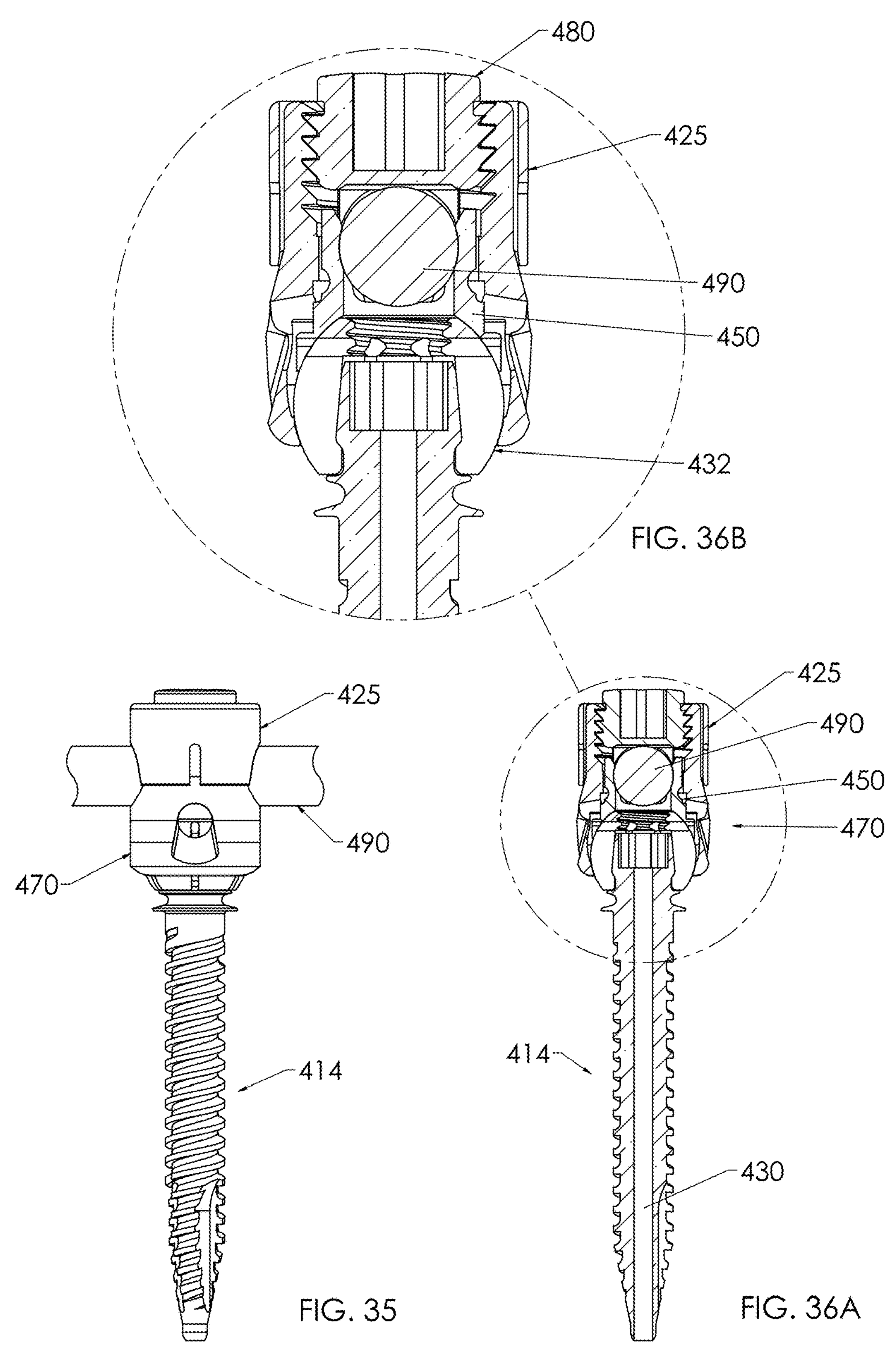
FIG. 35 is a side plane view of the retention clip screw.
FIG. 36A is a cross sectional view thereof.
FIG. 36B is a sectional view of FIG. 36A.

Referring now to FIGS. 27-36, illustrated is the modular screw assembly 400 with a retention clip. The pedicle screw 412 is formed from a shank 414 having an insertion end 416 and a connector end 418. The shank 414 having bone threads 420 graduating from the insertion end 416 to the connector end 418. The insertion end 416 may include a thread cut 422 to facilitate insertion into bone or spinal vertebrae. The connector end 418 having an outer surface 424 with a conical shape and an inner surface forming a driver receptacle 426.

The driver receptacle 426 is shaped for receipt of a driver tool allowing rotation of the shank. The driver receptacle 426 may be configured to accept a hexagonal socket, star drive, or other torque-transmitting interface that allows the shank 414 to be threaded to bone by rotation of the driver tool engaging the driver receptacle 426. In a preferred embodiment the shank includes a passageway 430 that can receive a positioning wire, not shown, for ease of shank placement.

A spherical shaped collet 432 is operatively associated with and securable to the connector end 418. The collet 432 having a plurality of compression slits 434 that extend from an upper portion 436 of the collet 432 through a lower edge 438 of the collet 432. The compression slits 434 allow the spherical ball 432 to be compressed around the connector end 424 for lockable securement. The collet 432 having an open upper passageway 440 extending to an open lower passageway 442, allowing insertion of a driver tool used to engage the receptacle 426.

A retention clip 450 having a chamfered lower inner edge 452 is positioned over the collet 432. A U-shaped receptacle 454 is formed by projections 456 and 458, constructed and arranged to capture a rod member during installation of the screw assembly 400.

A saddle 470 receives the clip 450 and couples to the collet 432. The saddle 470 having a U-shaped opening 472 with a lower section 474 for receipt of a rod member 490 and a threaded upper section 476 for receipt of a set screw 480. The set screw 480 having tool receptacle 482. Threads 484 engage the saddle threads 478. The threads 478 and 484 may consist of an interlocking thread to prevent splaying of the saddle when the set screw 480 is tightened.

A sleeve 425 is placed over the saddle 470 having an inner side wall 427 that fits over the outer surface 429 of the saddle 470. Tabs 421 and 423 extend inwardly from the inner side wall 427 and fit within the U-shaped saddle 470. By tightening the set screw 480, the sleeve further engages the rod member 490 for locking the saddle 470 in a fixed position relative to retention clip 450 the collet 432. The sleeve 425 prevents the saddle 470 from splaying should the set screw 480 be improperly torque tightened, or employs non-interlocking threads. The saddle 470 includes indentations 488 to hold with a tool while the set screw 480 is being torque tightening. The collet 432 and retention clip 450 providing a polyaxial attachment between the shank 414 and rod member 490. Once the rod member 490 has been positioned, the set screw 480 is tightened which locks saddle 470 to the collet 432 by applying pressure to the retention clip 450.

Figure 37:
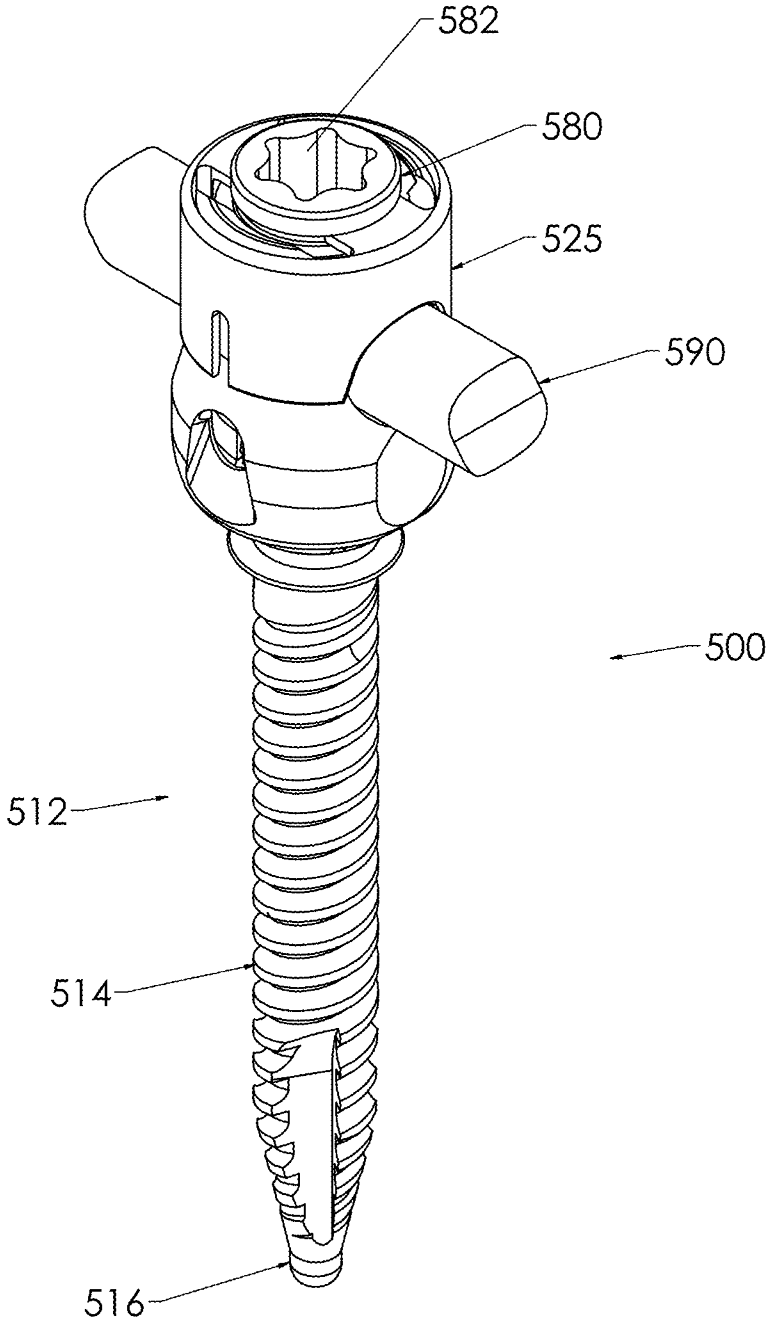
FIG. 37 is upper perspective view of a screw retention clip.
Figure 38:
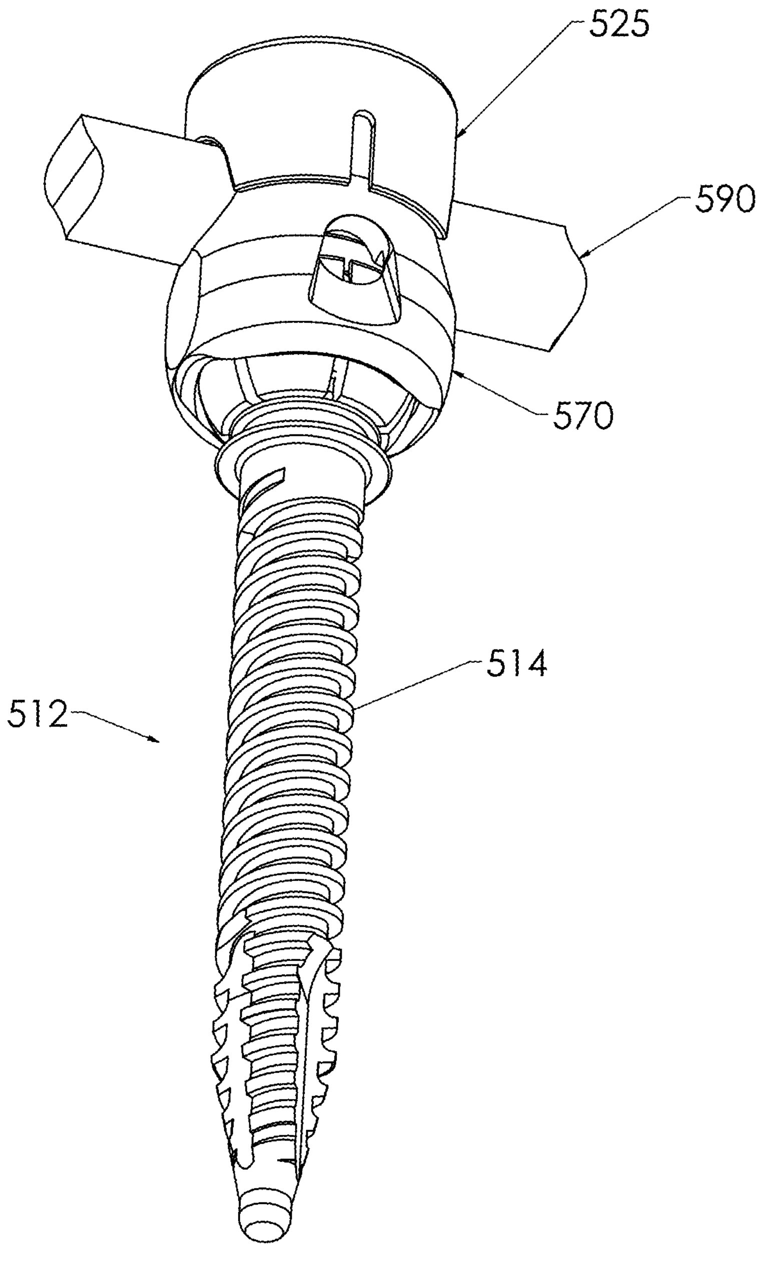
FIG. 38 is a lower perspective view thereof.
Figure 39:
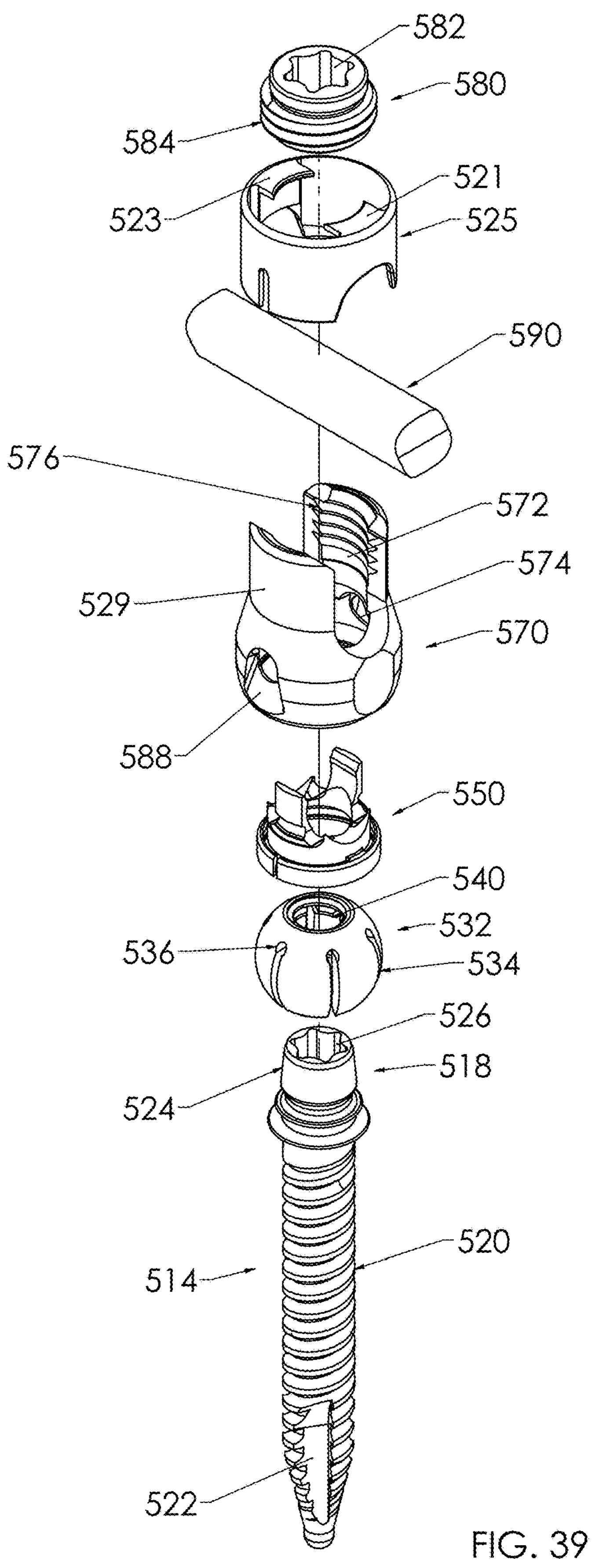
FIG. 39 is an upper perspective exploded front view thereof.
Figure 40:
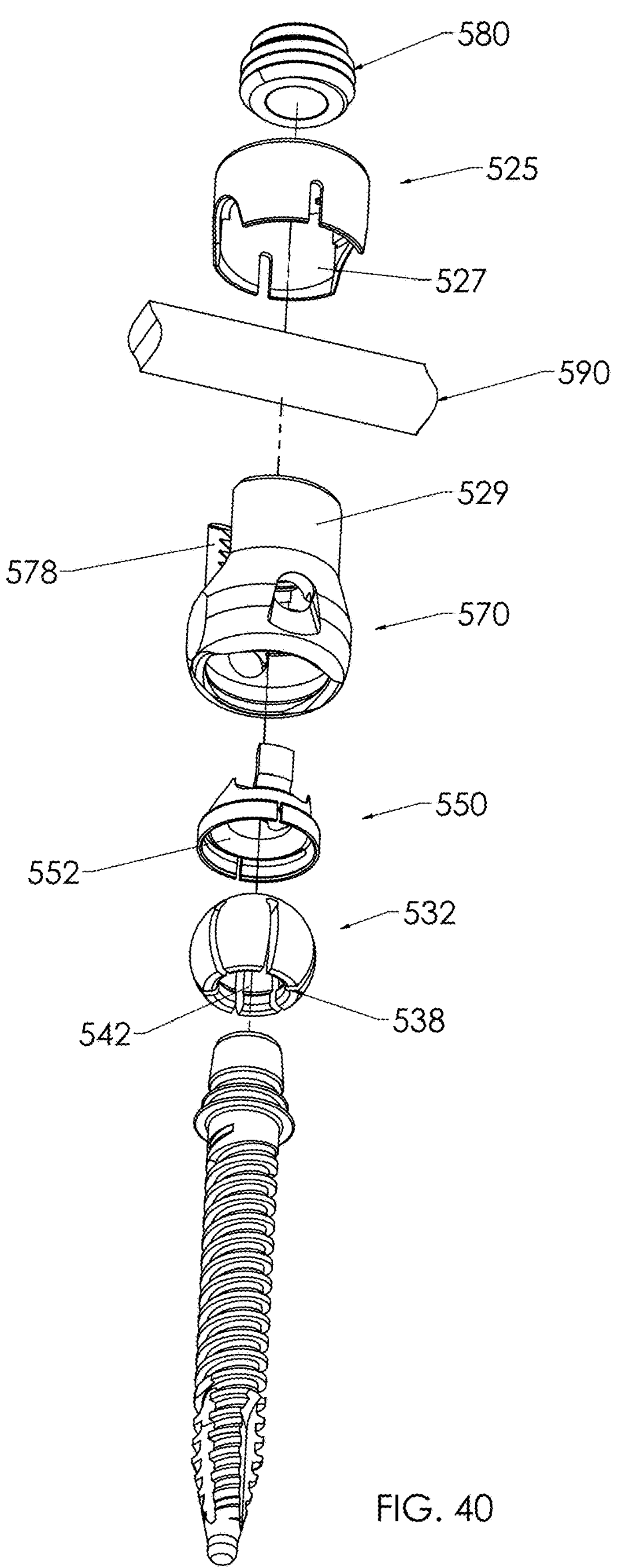
FIG. 40 is a lower perspective exploded rear view thereof.
Figure 41:
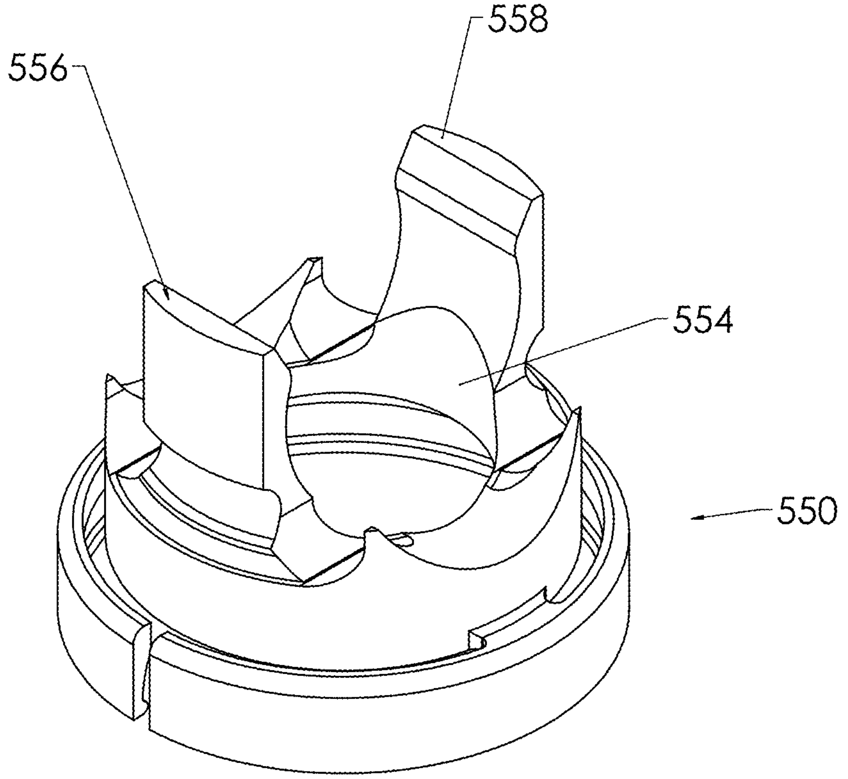
FIG. 41 is an upper perspective view of the retention clip.
Figure 42:
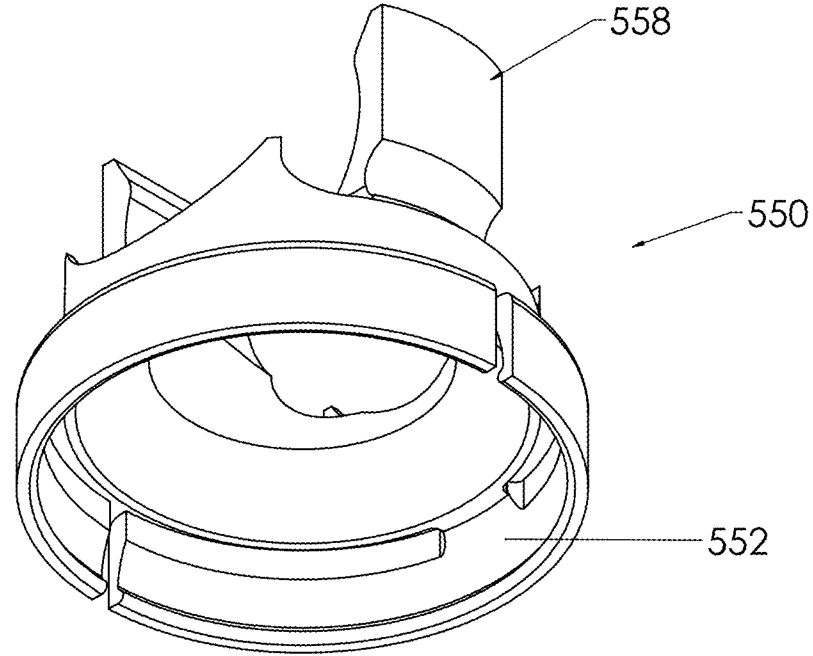
FIG. 42 is a lower perspective view of the retention clip.
Figures 43, 44A, 44B:
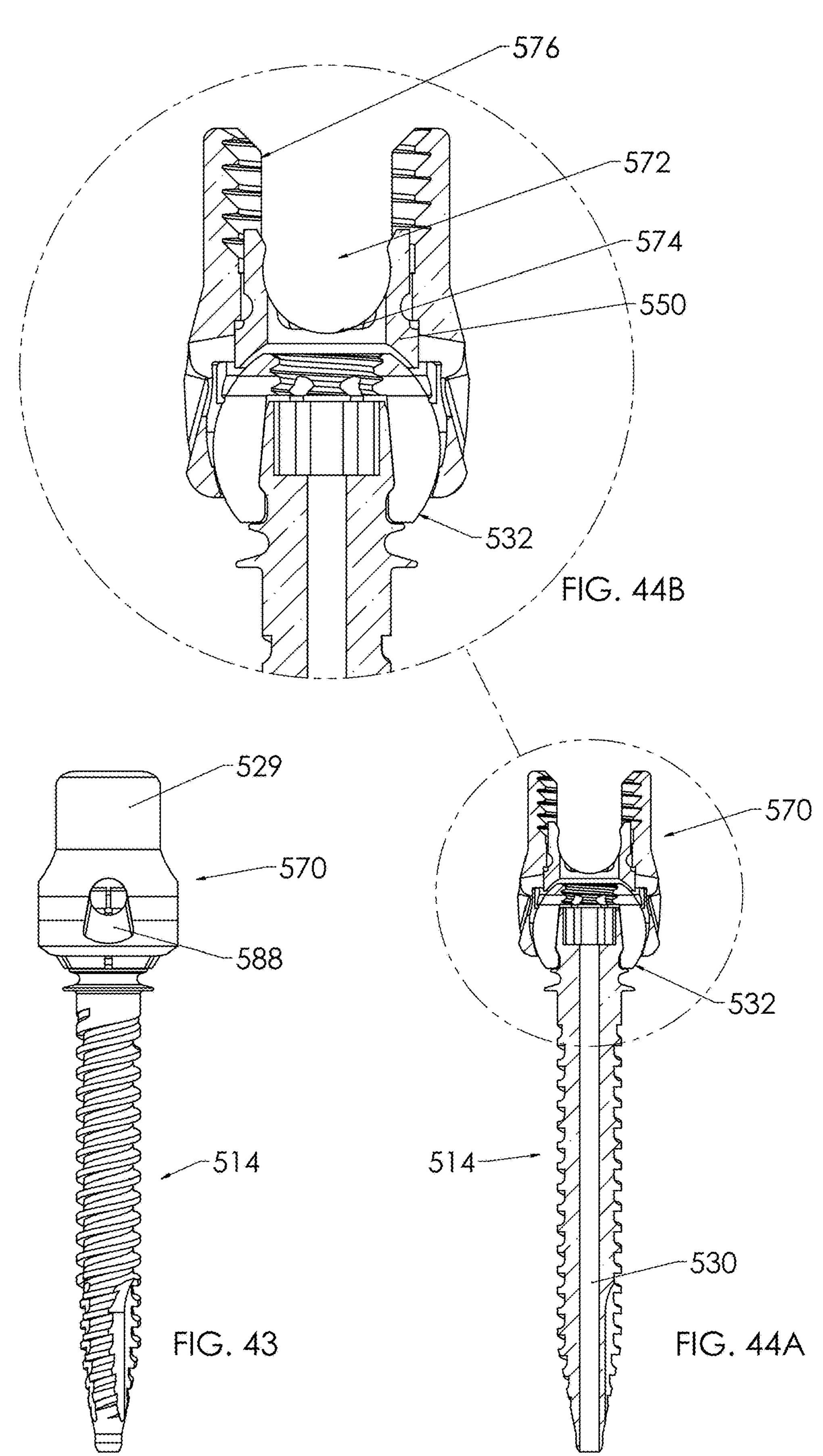
FIG. 43 is a front plane view of the retention clip screw.
FIG. 44A is a cross sectional view thereof.
FIG. 44B is a sectional view of FIG. 44A.
Figures 45, 46A, 46B:
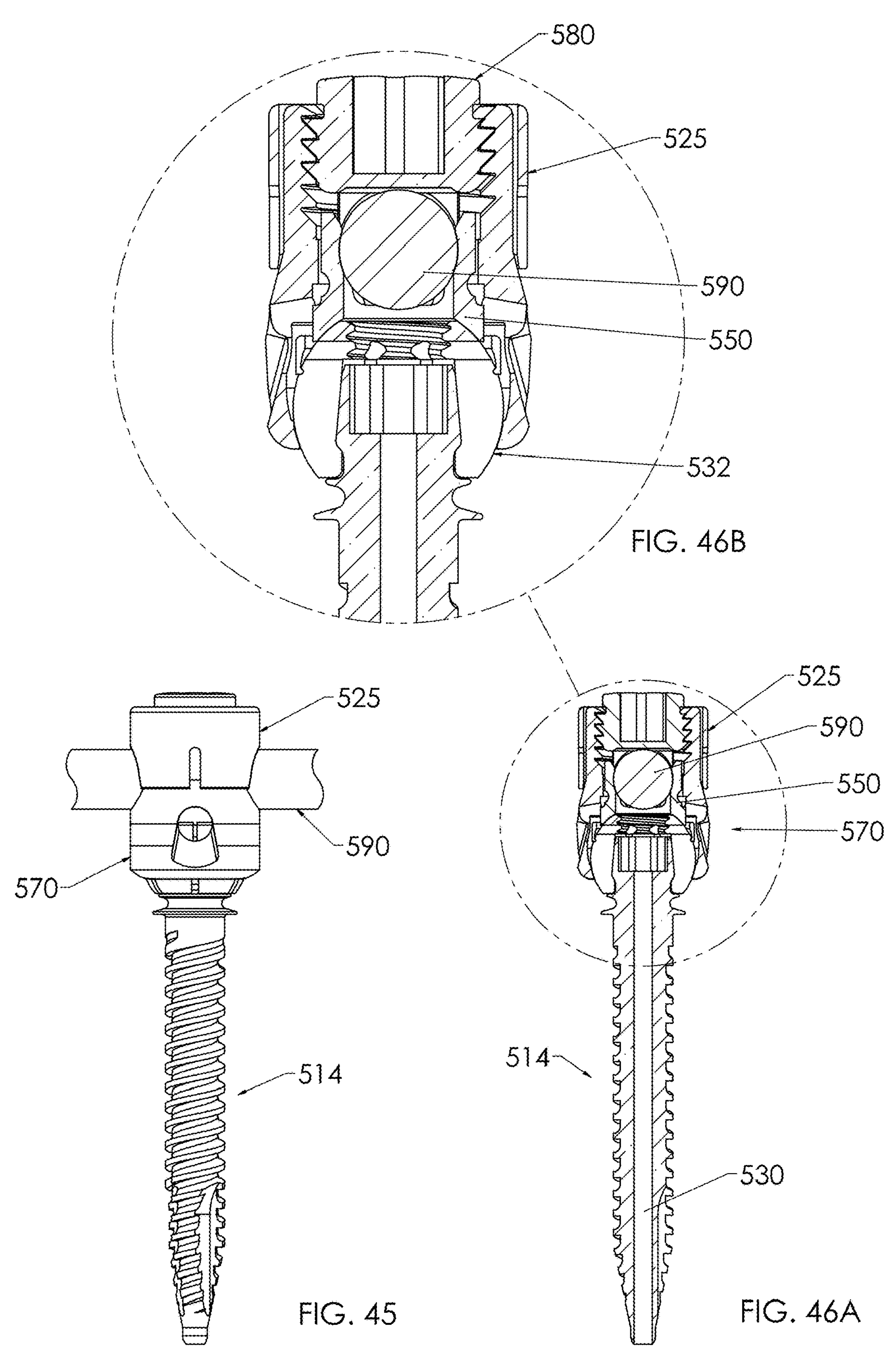
FIG. 45 is a side plane view of the retention clip screw.
FIG. 46A is a cross sectional view thereof.
FIG. 46B is a sectional view of FIG. 46A.

Referring now to FIGS. 37-46, illustrated is the modular screw assembly 500 with a retention clip. The pedicle screw 512 is formed from a shank 514 having an insertion end 516 and a connector end 518. The shank 514 having bone threads 520 graduating from the insertion end 516 to the connector end 518. The insertion end 516 may include a thread cut 522 to facilitate insertion into bone or spinal vertebrae. The connector end 518 having an outer surface 524 with a conical shape and an inner surface forming a driver receptacle 526.

The driver receptacle 526 is shaped for receipt of a driver tool allowing rotation of the shank. The driver receptacle 526 may be configured to accept a hexagonal socket, star drive, or other torque-transmitting interface that allows the shank 514 to be threaded to bone by rotation of the driver tool engaging the driver receptacle 526. In a preferred embodiment the shank includes a passageway 530 that can receive a positioning wire, not shown, for ease of shank placement.

A spherical shaped collet 532 is operatively associated with and securable to the connector end 518. The collet 532 having a plurality of compression slits 534 that extend from an upper portion 536 of the collet 532 through a lower edge 538 of the collet 532. The compression slits 534 allow the spherical ball 232 to be compressed around the connector end 524 for lockable securement. The collet 532 having an open upper passageway 540 extending to an open lower passageway 542, allowing insertion of a driver tool used to engage the receptacle 526.

A retention clip 550 having a split ring member 552 is positioned over the collet 532. An inner surface of the split ring member 552 may include lower and upper projections to provide collet engagement surfaces. A U-shaped receptacle 554 is formed by projections 556 and 558, constructed and arranged to capture a rod member during installation of the screw assembly 500. The split ring member 552 is used to facilitate secure locking of the rod member wherein the split ring 552 provides frictional engagement to screw head to maintain the saddle in position during placement. The projections 556 and 558 include ridges that allow a rod member to be snapped into position during placement.

A saddle 570 receives the clip 550 and couples to the collet 532. The saddle 570 having a U-shaped opening 572 with a lower section 574 for receipt of a rod member 590 and a threaded upper section 576 for receipt of a set screw 580. The set screw 580 having tool receptacle 582. Threads 584 engage the saddle threads 578. The threads 578 and 584 may consist of an interlocking thread to prevent splaying of the saddle when the set screw 580 is tightened.

A sleeve 525 is placed over the saddle 570 having an inner side wall 527 that fits over the outer surface 529 of the saddle 570. Tabs 531 and 533 extend inwardly from the inner side wall 527 and fit within the U-shaped saddle 570. By tightening the set screw 580, the sleeve further engages the rod member 590 for locking the saddle 570 in a fixed position relative to retention clip 550 the collet 532. The sleeve 525 prevents the saddle 570 from splaying should the set screw 580 be improperly torque tightened, or employs non-interlocking threads. The saddle 570 includes indentations 588 to hold with a tool while the set screw 580 is being torque tightening. The collet 532 and retention clip 550 providing a polyaxial attachment between the shank 514 and rod member 590. Once the rod member 590 has been positioned, the set screw 580 is tightened which locks saddle 570 to the collet 432 by applying pressure to the retention clip 550.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope.

Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The invention claimed is:

1. A modular pedicle screw assembly for use in spine surgery, comprising:

a shank having an insertion end configured for insertion into a vertebra, a connector end, and bone-engaging threads formed therebetween, the connector end having a conical outer surface and an inner driver receptacle configured to receive a driver tool for rotation of the shank;

a spherical collet securable to the connector end, the collet having a plurality of compression slits permitting compression of the collet for locking engagement with the connector end, the collet further having an open upper portion and an open lower portion to permit passage of the driver tool to the driver receptacle;

a split ring positioned over the collet, the split ring having a chamfered lower inner edge;

a cap having a lower surface conforming to a shape of the collet, said cap positioned within the split ring;

a saddle coupled to the collet, the saddle having a U-shaped channel defining a lower section configured to receive a rod member and a threaded upper section configured to receive a set screw;

wherein said shank is anchored to said saddle for receipt of a rod member, whereby tightening of the set screw compresses the cap and the split ring to lock the rod member and saddle in a fixed position relative to the shank.

2. The assembly of claim 1, wherein the shank includes a passageway extending from the insertion end toward the connector end, the passageway being sized to receive a positioning wire for guiding placement of the shank.

3. The assembly of claim 1, wherein the driver receptacle and a set screw receptacle comprises a hexagonal socket, star drive, or other torque-transmitting interface for engagement with a driver tool.

4. The assembly of claim 1, wherein the plurality of compression slits extend from the open upper portion of the collet toward the open lower portion of the collet to facilitate uniform compression to the connector end.

5. The assembly of claim 1, wherein the saddle, split ring, and cap each include a through-opening aligned with the open upper portion of the collet to permit insertion of a driver tool into the driver receptacle.

6. The assembly of claim 1, wherein the rod member is a spinal fixation rod.

7. The assembly of claim 1, wherein a polyaxial connection permits multi-directional angular adjustment of the rod member relative to the shank prior to tightening of the set screw.

8. The assembly of claim 1, wherein the conical outer surface of the connector end engages an inner surface of the collet to produce a friction fit when the collet is compressed.

9. The assembly of claim 1, wherein the cap is formed from a material having a hardness greater than that of the split ring to facilitate secure locking of the rod member, wherein said split ring provides frictional engagement to maintain the saddle in position during placement.

10. The assembly of claim 1, including a sleeve positioned over said saddle, said sleeve constructed and arranged to prevent expansion of saddle sidewalls.

11. The assembly of claim 1, wherein said saddle includes removable installation extensions.

12. The assembly of claim 1, wherein said collet provides polyaxial connection between the shank and the saddle.

13. The assembly of claim 1, wherein said collet provides a uniplanar connection between the shank and the saddle.

14. The assembly of claim 1, wherein said cap is a retention clip having a chamfered lower inner edge for placement over said collet, and a U-shaped receptacle formed by projections constructed and arranged to capture the rod member.

* * * * *